United States Patent
McGinley et al.

(10) Patent No.: US 12,178,977 B2
(45) Date of Patent: Dec. 31, 2024

(54) LAVAGE SYSTEMS AND DEVICES HAVING WARMING COMPONENT

(71) Applicant: CareFusion 2200, Inc., San Diego, CA (US)

(72) Inventors: Christopher McGinley, Highland Park, IL (US); John Krueger, Muskego, WI (US); Maleeha Mashiatulla, Glen Ellyn, IL (US); Dan Zimbler, Chicago, IL (US)

(73) Assignee: CareFusion 2200, Inc., San Diego, CA (US)

(*) Notice: Subject to any disclaimer, the term of this patent is extended or adjusted under 35 U.S.C. 154(b) by 18 days.

(21) Appl. No.: 17/501,739

(22) Filed: Oct. 14, 2021

(65) Prior Publication Data

US 2022/0118167 A1    Apr. 21, 2022

Related U.S. Application Data

(60) Provisional application No. 63/092,254, filed on Oct. 15, 2020.

(51) Int. Cl.
*A61M 3/02* (2006.01)

(52) U.S. Cl.
CPC ... *A61M 3/0245* (2013.01); *A61M 2202/0468* (2013.01); *A61M 2205/3368* (2013.01); *A61M 2205/364* (2013.01); *A61M 2205/366* (2013.01); *A61M 2205/584* (2013.01)

(58) Field of Classification Search
CPC ...... A61M 2205/366; A61M 2205/584; A61M 2205/3368; A61M 2202/0468; A61M 3/0245; A61M 3/0204; A61M 2205/36; A61M 1/369
See application file for complete search history.

(56) References Cited

U.S. PATENT DOCUMENTS

| | | | |
|---|---|---|---|
| 4,844,898 A | | 7/1989 | Komori et al. |
| 5,254,094 A | * | 10/1993 | Starkey .......... A61M 5/44 604/113 |
| 6,078,730 A | * | 6/2000 | Huddart .......... A61M 16/08 219/536 |
| 6,520,982 B1 | | 2/2003 | Boynton et al. |
| 6,824,528 B1 | | 11/2004 | Faries, Jr. et al. |
| 8,866,050 B2 | | 10/2014 | McBean et al. |

(Continued)

FOREIGN PATENT DOCUMENTS

WO    0024300 A2    5/2000

OTHER PUBLICATIONS

"Channel." Merriam-Webster.com Dictionary, Merriam-Webster, https://www.merriam-webster.com/dictionary/channel. Accessed Nov. 3, 2023. (Year: 2016).*

*Primary Examiner* — Philip R Wiest
*Assistant Examiner* — Matthew Wrubleski
(74) *Attorney, Agent, or Firm* — ARENTFOX SCHIFF LLP

(57) ABSTRACT

A system for applying a lavage fluid to a surface, the system having a body configured to house a lavage fluid, an application member in fluid communication with the body, the application member being configured to dispense the lavage fluid, and a warming component configured to communicate with the body so as to transfer energy from the warming component to the body sufficient to warm the lavage fluid housed in the body.

14 Claims, 19 Drawing Sheets

(56) References Cited

U.S. PATENT DOCUMENTS

| | | | |
|---|---|---|---|
| 9,855,398 B2* | 1/2018 | Klasek | A61M 16/0875 |
| 2003/0225441 A1* | 12/2003 | Boynton | A61F 7/00 |
| | | | 607/104 |
| 2008/0281268 A1* | 11/2008 | Vest Hansen | A61M 5/44 |
| | | | 604/113 |
| 2010/0016787 A1 | 1/2010 | Shapiro et al. | |
| 2013/0226087 A1* | 8/2013 | King | A61M 5/44 |
| | | | 604/113 |
| 2014/0276545 A1* | 9/2014 | Krogh Andersen | H05B 3/20 |
| | | | 604/114 |
| 2016/0081511 A1 | 3/2016 | Ackerman | |
| 2018/0093048 A1* | 4/2018 | Norman | A61M 5/445 |
| 2019/0015603 A1 | 1/2019 | Chassot et al. | |
| 2019/0143029 A1 | 5/2019 | Diwan | |

* cited by examiner

LAVAGE SYSTEMS AND DEVICES HAVING WARMING COMPONENT

CROSS-REFERENCE TO RELATED APPLICATION

This application claims priority to U.S. Provisional Application No. 63/092,254, filed Oct. 15, 2020, the disclosure of which is expressly incorporated herein by reference in its entirety.

TECHNICAL FIELD

The present disclosure is directed to devices and systems for applying a lavage fluid to a surface, and in particular, devices and systems comprising a warming component.

BACKGROUND

Currently, lavage (that is, the washing out of a body cavity, surgical cavity, or external wound with a medically acceptable fluid) is often employed to prevent contamination of an open surgical wound, which may occur for a variety of reasons such as accidental visceral entry or perforated viscus, operations complicated by gross spillage, departure from sterile technique, and/or existing, ongoing clinical infection. Lavage processes are thus often employed to provide intraoperative antiseptic wound irrigation.

The art of lavage currently embraces a wide variety of different approaches that vary based on the situation (for example, the size and shape of the cavity or wound) and on the medical practitioner performing the lavage process (for example, a practitioner's technique preference). Currently, no specific lavage technique is standard in the art, and as such, medical facilities often require numerous different lavage devices and systems to accommodate the variety of potential approaches. The presentation of such devices and systems is also sometimes a concern, as the inadvertently inappropriate use of such devices and systems (e.g., intravenously, if the device and/or system has a similar appearance to an intravenous device and/or system) could results in devastating effects.

Moreover, several drawbacks exist with current lavage practices, including insufficiencies in antiseptic fluid properties (e.g., the amount of time necessary for an antiseptic fluid to achieve an acceptable biological effect, which may be prohibitive), the risk of systemic absorption of the antiseptic fluid, adverse reactions such as anaphylaxis, peritoneal adhesions, neurotoxicity, and respiratory insufficiency, and improper dosage or contamination of the antiseptic fluid, which are sometimes prepared ad hoc by a medical practitioner performing the lavage.

In addition, lavage fluids often require a particular temperature in order to provide an acceptable function. For example, controlling the temperature of a patient during a surgical procedure is critical for achieving a positive patient outcome. As such, in the case wherein a lavage fluid is used prior to, during and/or after a surgical procedure, warming the lavage fluid is critical to ensure that the lavage fluid does not adversely impact the patient temperature during the procedure. In addition, over-warming of the lavage fluid may also cause deleterious effects on the patient and any sensitive tissue within the surgical cavity.

In current lavage practices, the temperature of the lavage fluid is typically controlled by providing the lavage fluid in a heating chamber or a water bath prior to use. However, as large volumes of lavage fluid are often used during lavage processes (e.g., the irrigation of a surgical cavity), this requires the lavage fluid to be placed in the heating chamber or water bath for a long period of time prior to use, which may create a significant challenge if there is not sufficient time to prepare the lavage fluid (i.e., in an emergency surgery) or if placement of the lavage fluid in the heating chamber or water bath is forgotten. In this case, the surgical procedure would either be delayed or proceed with a lavage fluid having an insufficient temperature. Moreover, lavage fluids used in current lavage practices cannot be indefinitely stored in current heating chambers and/or water baths, as thermal stress over an extended period of time can have a negative impact on the quality of the product (e.g., lavage fluid degradation and/or a reduced function of the container containing the lavage fluid). In addition, current lavage practices require availability of a heating chamber or water bath at or near the surgical area, which may pose space and/or sterility challenges. Finally, current lavage practices do not provide a reliable way for determining if and when a lavage fluid has reached an acceptable temperature.

There is thus a need in the art for versatile devices and systems for warming lavage fluids used in performing lavage processes, and in particular, devices and systems that enable medical practitioners to safely and effectively reduce contamination in surgical wounds that are susceptible to surgical site infections.

SUMMARY

The present disclosure is directed to devices and systems for delivering a lavage fluid, such as an antiseptic solution, to a surface. The device comprises a body that is configured to house a lavage fluid, such as an antiseptic solution, and is further configured to communicate with a warming component sufficient to raise and/or maintain the temperature of a lavage fluid contained in the body within an acceptable temperature range. The body is further configured to be in fluid communication with at least one application member, wherein the at least one application member is configured to apply the lavage fluid to a surface sufficient for a lavage process. The devices and systems may be adaptable such that a user may select from two or more different fluid flow rates, fluid flow patterns, and/or fluid flow forces, thus providing selectable control of lavage fluid delivery to a surface. The present disclosure is also directed to methods of using the devices and systems described herein.

DETAILED DESCRIPTION

Figure 1A:
FIG. 1A shows an example of a compressible body according to aspects of the present disclosure.

The present disclosure is directed to devices and systems for delivering a lavage fluid, such as an antiseptic solution, to a surface. The device comprises a body that is configured to house a lavage fluid, such as an antiseptic solution, and is further configured to communicate with a warming component sufficient to raise and/or maintain the temperature of a lavage fluid contained in the body within an acceptable temperature range. The body is further configured to be in fluid communication with at least one application member, wherein the at least one application member is configured to apply the lavage fluid to a surface sufficient for a lavage process. The devices and systems may be adaptable such that a user may select from two or more different fluid flow rates, fluid flow patterns, and/or fluid flow forces, thus providing selectable control of lavage fluid delivery. The present disclosure is also directed to methods of using the devices and systems described herein.

As used herein, the term "lavage fluid" refers to a fluid suitable for a lavage process as described herein. As used herein, "lavage" refers to the irrigation of a body cavity, a surgical cavity, and/or an external wound.

According to some aspects, the lavage fluid may comprise an antiseptic solution. As used herein, an "antiseptic solution" refers to a solution comprising at least a solvent and one or more antiseptic agents. According to some aspects, the antiseptic solution is an aqueous solution. As used herein, the term "aqueous solution" refers to a solution wherein the solvent comprises at least a majority of water. It should be understood that in some examples, the solvent may consist of water. According to some aspects, the antiseptic solution is an alcoholic solution. As used herein, the term "alcoholic solution" refers to a solution wherein the solvent comprises at least a majority of alcohol. It should be understood that in some examples, the solvent may consist of one or more alcohols. Non-limiting examples of alcohols include, but are not limited to, ethanol, isopropyl alcohol, n-propanol, and combinations thereof.

In one non-limiting example, the antiseptic agent may comprise a cationic molecule (i.e., a molecule having a positive charge), such as a cationic surfactant or a cationic biguanide derivative (i.e., a compound derived from biguanide). According to some aspects, the antiseptic agent may comprise a bis-(dihydropyridinyl)-decane derivative (i.e., a compound derived from bis-(dihydropyridinyl)-decane). According to some aspects, the antiseptic agent may comprise an octenidine salt and/or a chlorhexidine salt. According to some aspects, the antiseptic agent may comprise alexidine, octenidine dihydrochloride, chlorhexidine gluconate, or a combination thereof.

Additionally or alternatively, the antiseptic agent may comprise iodine. According to some aspects, the iodine may be provided as an iodine complex, such as povidone-iodine (PVPI), nonylphenoxy-(ethyleneoxy)-iodine, polyethylene oxy polyprop leneoxy-iodine, undecoylinium-chloride-iodine, iodine povacrylex, and combinations thereof.

Additionally or alternatively, the antiseptic agent may comprise an oxidant (i.e., an oxidizing agent). Non-limiting examples of oxidants according to the present disclosure include, but are not limited to, sodium hypochlorite, hydrogen peroxide, and combinations thereof.

The antiseptic agent may have an antimicrobial activity sufficient to provide an acceptable log reduction of microbes in a certain time period. It should be understood that as used herein, the term "microbes" may refer to any microorganism to be killed and/or removed as a result of lavage. Example microbes include bacteria, fungi, viruses, and combinations thereof.

Example bacteria include, but are not limited to, *Streptococcus mutans, S. pyogenes* (group A β-hemolytic streptococci), *S. salivarius, S. sanguis, Staphylococcus aureus S. epidermidis, S. haemolyticus, S. hominis, S. simulans, S. saprophyticus*, methicillin/oxacillin-resistant (MRSA/ORSA) and methicillin/oxacillin-susceptible Staphylococci (MSSA/OSSA), *Enterococcus* (e.g., *E. faecalis E. faecium*, and *E. hirae*), vancomycin-resistant *Enterococcus* (VRE) and vancomycin-susceptible *Enterococcus* (VSE), *Bacteroides fragilis, Propionibacterium acnes, Clostridium difficile* (spore and vegetative cells), *Selenomonas, Pseudomonas aeruginosa, Escherichia coli, Burkholderia cepacia, Proteus mirabilis, Gardnerella vaginalis, Klebsiella aerogenes, K. pneumoniae, K. pneumoniae* multidrug resistant (MDR), *Acinetobacter baumannii, A. baumannii* MDR, *Achromobacter xylosoxidans. Micrococus luteus, Ralstonia pickettii, Haemophilus influenza,* and *Serratia marcescens*

Example fungi include, but are not limited to, *Aspergillus niger, Candida albicans, C. aurus, C. dubliniensis, C. glabrata* (formerly *Torulopsis glabrata*), *C. guillermondii, C. kefyr* (formerly *C. pseudotropicalis*), *C. krusei, C. lusitaniae, C. tropicalis, Epidermophyton floccosum, Microsporum gypseum, M. canis,* and *Trichophyton mentagrophytes*

Example viruses include, but are not limited to, those having a lipid component in their outer coat or have an outer envelope such as cytomegalovirus (CMV), human immunodeficiency virus (HIV), herpes simplex virus types 1 (HSV-1) and 2 (HSV-2), influenza virus, parainfluenza virus, variola virus (smallpox virus), vaccinia, norovirus, and coronavirus According to some aspects, the certain time period may be a period of no more than about five minutes, optionally no more than about four minutes, optionally no more than about three minutes, optionally no more than about two minutes, and optionally no more than about one minute.

According to some aspects, the certain time period may be no more than about 120 seconds, optionally no more than about 105 seconds, optionally no more than about 90 second, optionally no more than about 75 seconds, optionally no more than about 60 seconds, optionally no more than about 45 seconds, optionally no more than about 30 seconds, and optionally no more than about 15 seconds.

It should be understood that "an acceptable log reduction" may be microbe-dependent. For example, an acceptable log reduction as described herein may refer to an acceptable log reduction of one type of microbe present on a surface (e.g., present in a body cavity or at an external wound site), a combination of two more types of microbes present on a surface, or total microbes present on a surface.

According to some aspects, an acceptable log reduction may be at least about 1.0, optionally at least about 1.1, optionally at least about 1.2, optionally at least about 1.3, optionally at least about 1.4, optionally at least about 1.5, optionally at least about 1.6, optionally at least about 1.7, optionally at least about 1.8, optionally at least about 1.9, optionally at least about 2.0, optionally at least about 2.1, optionally at least about 2.2, optionally at least about 2.3, optionally at least about 2.4, optionally at least about 2.5, optionally at least about 2.6, optionally at least about 2.7, optionally at least about 2.8, optionally at least about 2.9, optionally at least about 3.0, optionally at least about 3.1, optionally at least about 3.2, optionally at least about 3.3, optionally at least about 3.4, optionally at least about 3.5, optionally at least about 3.6, optionally at least about 3.7, optionally at least about 3.8, optionally at least about 3.9, optionally at least about 4.0, optionally at least about 4.1, optionally at least about 4.2, optionally at least about 4.3, optionally at least about 4.4, optionally at least about 4.5, optionally at least about 4.6, optionally at least about 4.7, optionally at least about 4.8, optionally at least about 4.9, and optionally at least about 5.0.

According to some aspects, the antiseptic agent may be present in the antiseptic solution in a concentration sufficient to provide an acceptable log reduction of microbes in a certain time period as described herein. According to some aspects, the antiseptic agent may be present in the antiseptic solution at a concentration of between about 0.001 and 5% w/v, optionally between about 0.001 and 2.5% w/v, optionally between about 0.001 and 1% w/v, optionally between about 0.001 and 0.1% w/v, optionally between about 0.001 and 0.01% w/v, optionally between about 0.01 and 5% w/v, optionally between about 0.01 and 2.5% w/v, optionally between about 0.01 and 2% w/v, optionally between about 0.01 and 1.5% w/v, optionally between about 0.01 and 1% w/v, and optionally about 0.5% w/v.

According to some aspects, the antiseptic agent may be present in the antiseptic solution at a concentration of between about 0.1 and 0.9% w/v, optionally between about 0.2 and 0.8% w/v, optionally between about 0.3 and 0.7% w/v, and optionally between about 0.4 and 0.6% w/v.

According to some aspects, the antiseptic agent may be present in the antiseptic solution at a concentration of between about 0.1 and 1% w/v, optionally between about 0.2 and 1% w/v, optionally between about 0.3 and 1% w/v, and optionally between about 0.4 and 1% w/v.

It should be understood that according to some aspects, the lavage fluid is not necessarily an antiseptic solution as described herein and may be any medically acceptable fluid configured to perform a lavage process as described herein. In one non-limiting example, the lavage fluid may comprise a saline solution. The saline solution may comprise water and sodium chloride in a medically acceptable concentration, such as between about 0.1 and 1%, w/v, optionally about 0.45% w/v, and optionally about 0.9% w/v.

According to some aspects, the lavage fluid, such as an antiseptic solution as described herein, may comprise a visualizing aid. As used herein, the term "visualizing aid" refers to a component in a lavage fluid configured to aid in visualizing the application of the lavage fluid. Example visualizing agents include, but are not limited to, tinting agents, staining agents, and radiopaque agents. It should be understood that the visualizing agent may be the same as or different from one of the other components of the lavage fluid. For example, the antiseptic agent may function as a visualizing agent. Additionally or alternatively, the lavage fluid may comprise a visualizing agent that is disparate from the antiseptic agent.

According to some aspects, the lavage fluid may comprise a tinting agent. As used herein, the term "tinting agent" refers to a component sufficient to provide an observable color to a fluid. The tinting agent may be sufficient to allow visualization of the lavage fluid upon application to a surface. In some non-limiting examples, the tinting agent may comprise an anionic tinting agent, such as an anionic dye. The anionic dye may be any dye suitable for medical use, such as dyes approved by the Food and Drug Administration for use in food, drugs, and/or cosmetics (i.e., "D&C" or "FD&C" dyes). Example anionic dyes include, but are not limited to, FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Fluorescein), D&C Orange No. 4, and combinations thereof. Combinations may be implemented to arrive at a particular color. For example, an orange tint may comprise both FD&C Red No. 40 and D&C Yellow No. 8. Additionally or alternatively, the tinting agent may comprise a chemical compound that is observable upon exposure to visible and/or non-visible light, including, but not limited to, vitamin B-12, medical honey, fluorescent polymeric nanoparticles, water soluble luminescent carbon nanodots, quinine, and combinations thereof.

According to some aspects, the lavage fluid, such as an antiseptic solution as described herein, may comprise a staining agent. As used herein, the term "staining agent" refers to a component sufficient to temporarily or permanently color a surface with which it comes in contact.

According to some aspects, the lavage fluid, such as an antiseptic solution as described herein, may comprise a radiopaque agent. As used herein, the term "radiopaque agent" refers to a component that is opaque to the radio wave and x-ray portion of the electromagnetic spectrum sufficient for visualization. In some non-limiting examples, the radiopaque agent may comprise barium, iodine, iron oxide nanoparticles, gadolinium complex nanospheres, silica nanospheres, and combinations thereof.

According to some aspects, the lavage fluid, such as an antiseptic solution as described herein, may be basic, neutral, or acidic. According to some aspects, the lavage fluid may have a pH of between about 1 and 8, optionally between about 1 and 7, optionally between about 1 and 6, and optionally between about 2 and 5.5.

According to some aspects, the lavage fluid, such as an antiseptic solution as described herein, may comprise a buffer system. As used herein, the term "buffer system" refers to a component present in a composition or solution which may provide a resistance to significant change in pH caused by a strong acid or base. A buffer system may comprise a single agent or more than one agent, such as a weak acid and its conjugate base. A buffer system may provide a resistance to a significant pH change by interacting with a strong acid or strong base in a composition or solution, thereby at least partially preventing the pH of the composition or solution from changing significantly.

Generally, a buffer system has one or more buffer ranges wherein the buffer system has the ability to provide resistance to significant pH change. When a composition or solution comprising the buffer system has a pH inside the buffer system's buffer range, the pH of the composition or solution will not change significantly with the addition of equimolar amounts of a strong acid or strong base.

The buffer range of a buffer system is related to the acid dissociation constant ($K_a$) of one or more weak acids comprised by the buffer system. The term "acid dissociation constant" refers to the equilibrium constant of a dissociation reaction of an acid. The midpoint of a buffer range for a buffer system is generally about the logarithmic measure of the acid dissociation constant (i.e., the $pK_a$, equal to $-\log_{10} K_a$) of a weak acid comprised by the buffer system.

According to some aspects, the lavage fluid, such as an antiseptic solution as described herein, may comprise a stabilizing agent. As used herein, the term "stabilizing agent" refers to any component that supports the stability of a lavage fluid not otherwise explicitly described herein.

The device according to the present disclosure comprises a body configured to contain a lavage fluid as described herein. According to some aspects, the body may be compressible. As used herein, the term "compressible" refers to the ability to reversibly reduce in volume without unacceptable changes, such as an unacceptable permanent change to size, to shape, and/or to one or more of the properties as described herein. According to some aspects, the body may be configured such that upon compression, at least a portion of the antiseptic agent contained therein is dispensed. It should be understood that as used herein, "dispense" (alternatively referred to as "discharge") may refer to transferring the lavage fluid to an application member in fluid communication with the body and/or it may refer to transferring the lavage fluid from an application member to a surface.

According to some aspects, the body may be collapsible. As used herein, the term "collapsible" refers to the ability to permanently reduce in volume. For example, a collapsible body as described herein may have a first volume when a first volume of fluid is contained therein. When at least a portion of the fluid is dispensed, the collapsible body may collapse to have a second volume, the second volume being less than the first volume. It should be understood that a collapsible body will advantageously reduce the volume of waste (e.g., the volume of the body after the fluid therein has been dispensed). A collapsible body may further provide for a more efficient fluid discharge.

According to some aspects, the body may be configured to allow at least a 10% reduction in volume when compressed and/or collapsed, optionally at least a 20% reduction in volume, optionally at least a 30% reduction in volume, optionally at least a 40% reduction in volume, optionally at least a 50% reduction in volume, optionally at least a 60% reduction in volume, optionally at least a 70% reduction in volume, optionally at least a 80% reduction in volume, optionally at least a 90% reduction in volume, and optionally at least a 99% reduction in volume.

According to some aspects, the body may comprise a body material that is compatible with the lavage fluid contained therein, that is, a material that does not chemically or physically react with the lavage fluid or otherwise render the lavage fluid unfit for medical use.

According to some aspects, the body material may be sufficient to prevent unacceptable vapor or antiseptic loss from a lavage fluid contained therein over a certain period of shelf life. It should be understood that "unacceptable vapor or antiseptic loss" may be a loss that results in the lavage fluid becoming unsuitable for its intended use. Vapor or antiseptic loss may result from, for example, adsorption or absorption of the antiseptic by a material (e.g., by the body material), evaporation of solution, evaporation of a component of a solution (e.g., an antiseptic agent of an antiseptic solution), or a combination thereof. In one non-limiting example wherein the lavage fluid comprises water and iodine as described herein, the body material may be sufficient to prevent water vapor loss and/or iodine loss over a certain period of shelf life.

As used throughout this application, the term "shelf life" refers to the length of time that a product (e.g., an antiseptic solution) may be stored while remaining within the specifications required for the form, fit, and function of the product. Shelf life may be determined by measuring certain characteristics of the product that may indicate that the product is unfit for medical use. For example, shelf life may be determined by measuring the concentration of impurities in the product, the color change of the product, the concentration of insoluble particles in the product, the potency of an active agent contained by the product (e.g., an antiseptic agent), the concentration of one or more components of the product, the pH of the product, and/or the sterility of the product after storage in long-term storage conditions. As used herein, the term "long-term storage conditions" refers to environmental conditions sufficient for a product to be acceptably stored for more than 72 hours. According to some aspects, long-term storage conditions may refer to a temperature of about 25° C. and a relative humidity of about 60%. Additionally or alternatively, shelf life may be determined by measuring the concentration of impurities in the product, the color change of the product, the concentration of insoluble particles in the product, the potency of an active agent of the product, the concentration of one or more components of the product, the pH of the product, and/or the sterility of the product after storage at 37° C. and 65% relative humidity. Additionally or alternatively, shelf life may be determined by measuring the concentration of impurities in the product, the color change of the product, the concentration of insoluble particles in the product, the potency of an active agent of the product, the concentration of one or more components of the product, the pH of the product, and/or the sterility of the product after storage at between about 15 and 30° C., with excursions at a temperature of no more than about 40° C.

According to some aspects, the period of shelf life may be at least about 20 months, optionally at least about 21 months, optionally at least about 22 months, optionally at least about 23 months, optionally at least about 24 months, optionally at least about 25 months, optionally at least about 26 months, optionally at least about 27 months, optionally at least about 28 months, optionally at least about 29 months, optionally at least about 30 months, optionally at least about 31 months, optionally at least about 32 months, optionally at least about 33 months, optionally at least about 34 months, optionally at least about 35 months, optionally at least about 36 months, optionally at least about 37 months, optionally at least about 38 months, optionally at least about 39 months, and optionally at least about 40 months.

According to some aspects, the body material may be sufficient for sterilization by any known sterilization techniques useful according to the present disclosure, including moist heat sterilization (i.e., autoclaving), gas sterilization, gamma irradiation, electron-beam (e-beam) sterilization, aseptic manufacturing processes (e.g., aseptic filtration and/ or blow-fill-seal operations), and combinations thereof. According to some aspects, a body material may be determined to be sufficient for sterilization if a container comprising the body material has a Sterility Assurance Level (SAL) of at least $10^{-6}$ after sterilization and provides an acceptable result upon integrity testing for the container closure after sterilization.

According to some aspects, the body material may have a sufficient mechanical strength such that the body provides an acceptable response to impact, vibration, shaking, or a combination thereof. According to some aspects, an acceptable response refers to a response compliant with ASTM D4169-16 (Standard Practice for Performance Testing of Shipping Containers and Systems), ASTM D4728-06 (Standard Test Method for Random Vibration Testing of Shipping Containers), ASTM D642-15 (Standard Test Method for Determining Compressive Resistance of Shipping Containers, Components, and Unit Loads), or any combination thereof. According to some aspects, the body material may be safe for biomedical use. For example, the body material may comply with ISO 10993 and/or with REACH requirements. According to some aspects, the body material may be sufficient to exhibit at least a portion of the characteristics described herein over a certain period of the lavage fluid's shelf life at a temperature of between about 15 and 30° C., with excursions at a temperature of no more than about 40° C. Additionally or alternatively, the body material may be sufficient to exhibit at least a portion of the characteristics described herein over a certain period of the lavage fluid's shelf life after storage at about 25° C. and 60% relative humidity. Additionally or alternatively, the body material may be sufficient to exhibit at least a portion of the characteristics described herein over a certain period of the lavage fluid's shelf life after storage at about 37° C. and 65% relative humidity.

The body material may be rigid or flexible. As used herein, the term "rigid" refers to a stiffness sufficient to resist deformation upon normal operating forces. As used herein, the term "flexible" refers to the ability to bend or compress under normal operating forces.

Example body materials include, but are not limited to, glass, plastic, paper, foil, and any combination thereof. Example plastics useful according to the present disclosure include, but are not limited to, high-density polyethylene (HDPE), low-density polyethylene (LDPE), polypropylene, polystyrene, nylon, and any combination thereof. According to some aspects, the body material may be a lined and/or coated material, such as a lined and/or coated paper.

Figure 4:
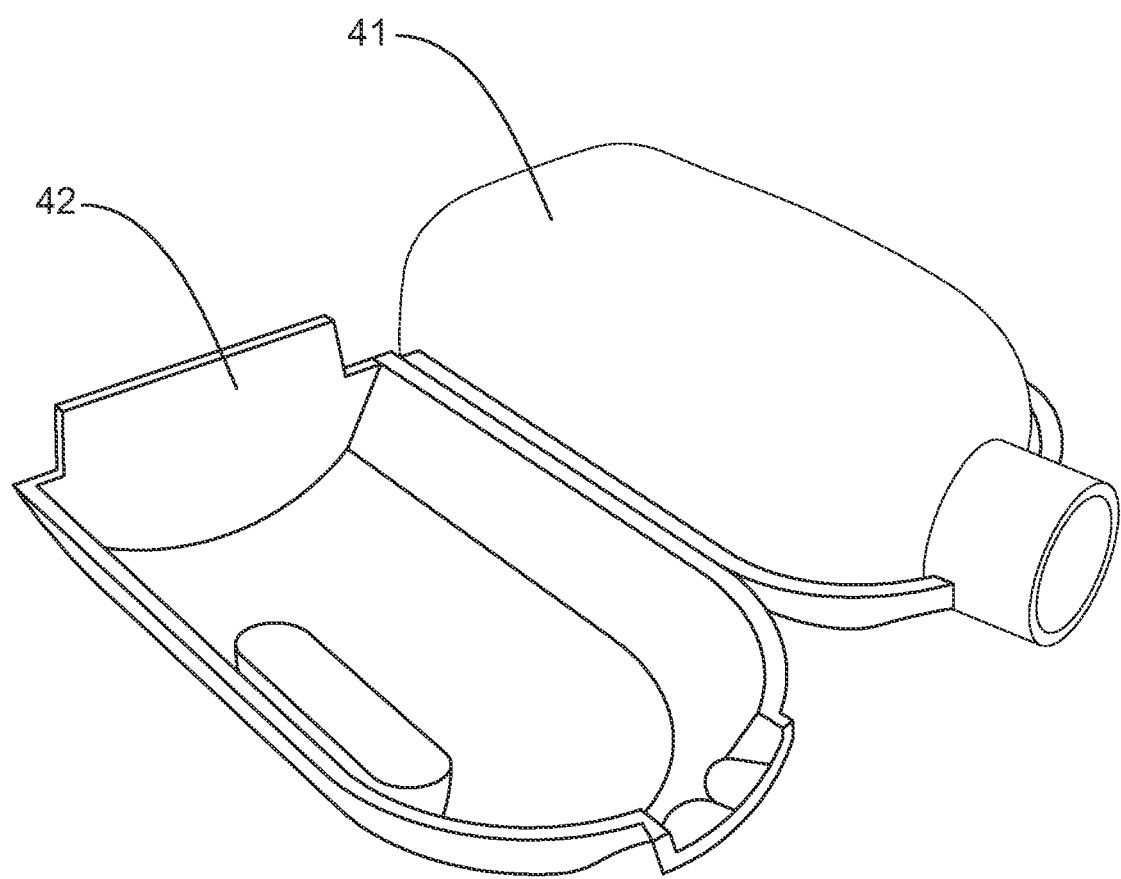
FIG. 4 shows an example of a body with an outer casing according to aspects of the present disclosure.

According to some aspects, the body may be provided with an outer casing. For example, FIG. 4 shows a body 41 comprising a flexible body material. Body 41 may be provided with an outer casing 42, which may be permanent or removable in relation to body 41. According to some aspects, outer casing 42 may be rigid, thus functioning to protect body 41 during storage and/or use. Outer casing 42 may additionally or alternatively function to distinguish body 41 from similar devices used in medical settings, such as intravenous (IV) fluid bags. In this way, outer casing 42 may reduce the risk of inadvertent misuse of body 41.

Figure 1B:
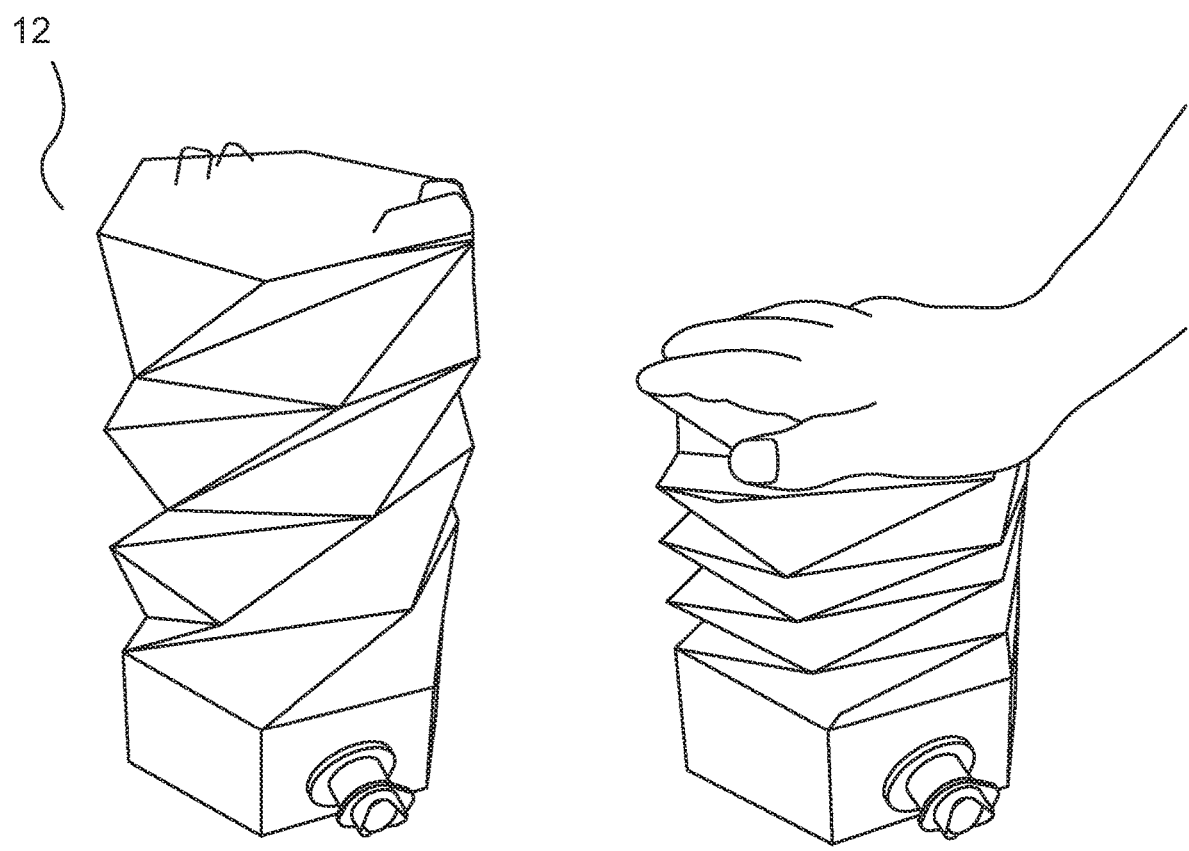
FIG. 1B shows an example of a collapsible body according to aspects of the present disclosure.

The body according to the present disclosure is configured to dispense a lavage fluid, such as an antiseptic solution, contained therein via one or more mechanisms. According to some aspects, the body may be configured to dispense the lavage fluid upon compression as described herein. For example, as shown in FIG. 1A, body 11 may be configured to dispense at least a portion of the lavage fluid contained therein in response to compression, such as squeezing. Additionally or alternatively, body 12 may be configured to dispense at least a portion of the lavage fluid contained therein in response to longitudinal compression, as shown in FIG. 1B.

Figure 2A:
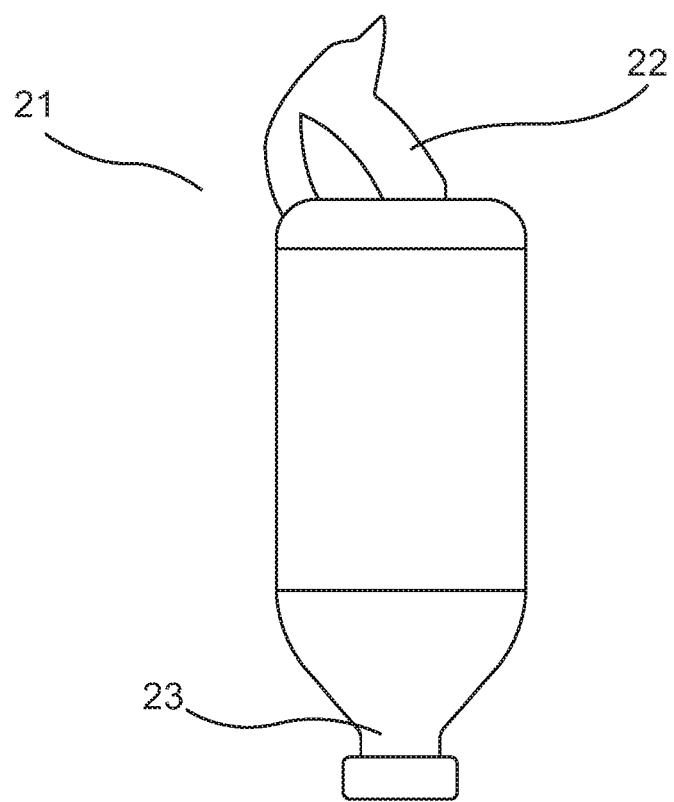
FIG. 2A shows an example of a body according to aspects of the present disclosure.

Additionally or alternatively, the body may be configured to dispense at least a portion of the lavage fluid contained therein upon orienting the body in a certain orientation. For example, as shown in FIG. 2A, body 21 may comprise an aperture 23 through which lavage fluid may be dispensed. In this example, body 21 may be configured such that when provided in a certain orientation (e.g., wherein aperture 23 is provided at or near the bottom of the body in relation to the ground), at least a portion of the lavage fluid is dispensed by the force of gravity.

In the example shown in FIG. 2A, body 21 may comprise a positioning component 22 that allows the body to be arranged in a certain orientation. The positioning component 22 may be any component configured to position and/or fix the body in a selected orientation, such as a hook, strap, snap, button, tie, or combination thereof. The positioning component 22 may be integral to the body and/or may be a separate component configured to interact with the body, such as a strap attachable to the body. The positioning component 22 may be configured to interact with a second positioning component, such as an extension arm configured to interact with a hook comprised by and/or attached to the body.

Figure 2B:
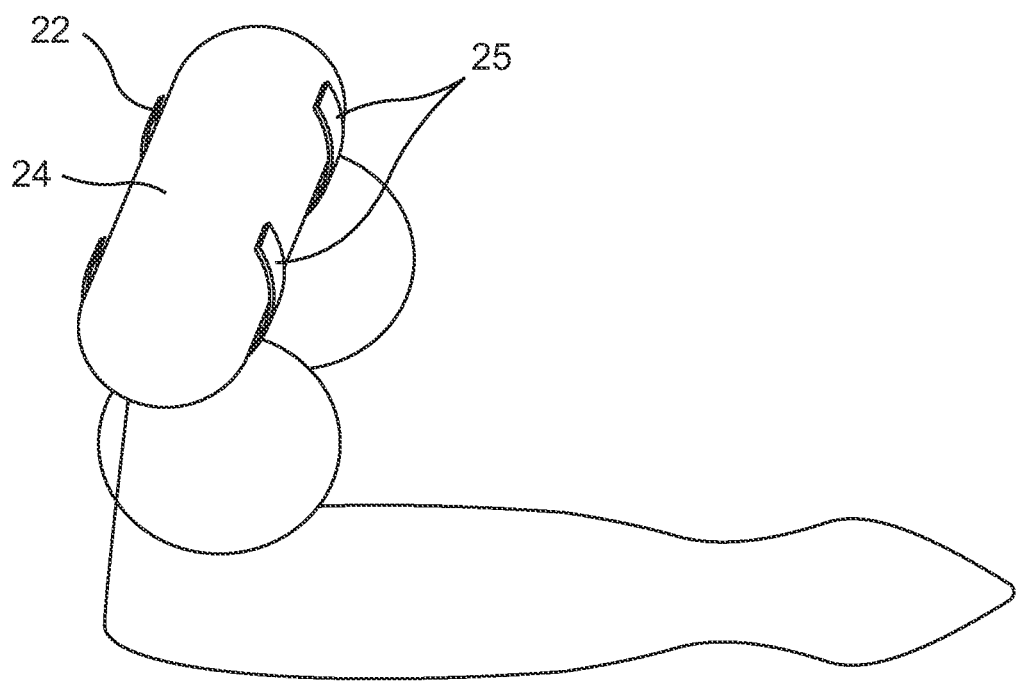
FIG. 2B shows an example of a body according to aspects of the present disclosure.

FIG. 2B shows another example of a system according to the present disclosure. In this example, body 24 is configured to interact with a separate positioning component 22, which may comprise, for example, snaps 25. In this way, body 24 may be positioned relative to and fixed to a user's arm, such as the arm of a medical practitioner performing lavage. In this example, lavage fluid may be dispensed by the force of gravity as described herein and/or by a dispensing aid as will be described herein.

According to some aspects, the body may be configured to communicate with a dispensing aid, wherein the dispensing aid is configured to provide a force sufficient to at least partially dispense the lavage fluid contained in the body. For example, the dispensing aid may comprise a pump configured to move the lavage fluid from the body. The pump may be a mechanical pump, a motorized pump, a vacuum pump, or any combination thereof.

It should be understood that the body may be configured to dispense the lavage fluid via one or a combination of the mechanisms as described herein. For example, the body may be configured to dispense the lavage fluid upon compression in conjunction with the force of gravity. Additionally or alternatively, the body may be configured to dispense the lavage fluid upon compression and/or by the force of gravity in conjunction with the force created by the pump (including, but not limited to, a vacuum force created by the pump). According to some aspects, the body may be configured to selectably dispense the lavage fluid via one or more of the mechanisms as described herein. In one non-limiting example, the body may be configured to dispense the lavage fluid upon compression both with and without the force of a pump. In this way, the user may select a desired delivery mechanism based on physical limitations (e.g., the physical capabilities of the user), a desired fluid flow force, a desired fluid flow rate, a desired fluid flow pattern (e.g., pulsed or constant), or a combination thereof.

According to some aspects, the body may be configured to dispense at least about 75% of the lavage fluid contained therein, optionally at least about 80%, optionally at least about 85%, optionally at least about 90%, optionally at least about 95%, and optionally about 100%. The body may be configured to continually dispense the lavage fluid and/or to intermittently dispense the lavage fluid. In one non-limiting example, the body may be configured to intermittently dispense the lavage fluid such that the lavage fluid is only dispensed upon compression of the body and/or upon actuation of a dispensing aid such as a pump.

The body may be configured to contain a volume of lavage fluid sufficient to perform at least a portion of a lavage process. According to some aspects, the body may be configured to contain between about 250 and 2000 mL of fluid, and optionally between about 500 and 1000 mL. According to some aspects, the body may be configured to contain about 500 mL of fluid. According to some aspects, the body may be configured to contain about 1 L of fluid.

According to some aspects, the body may be configured to communicate with a warming component sufficient to warm a lavage fluid contained in the body to a temperature within an acceptable temperature range and/or maintain a lavage fluid contained in the body at a temperature within an acceptable temperature range. The warming component may comprise at least one surface configured to contact a corresponding surface of the body sufficient to transfer energy to the body and subsequently a lavage fluid contained in the body, thus warming the lavage fluid.

Figure 13:
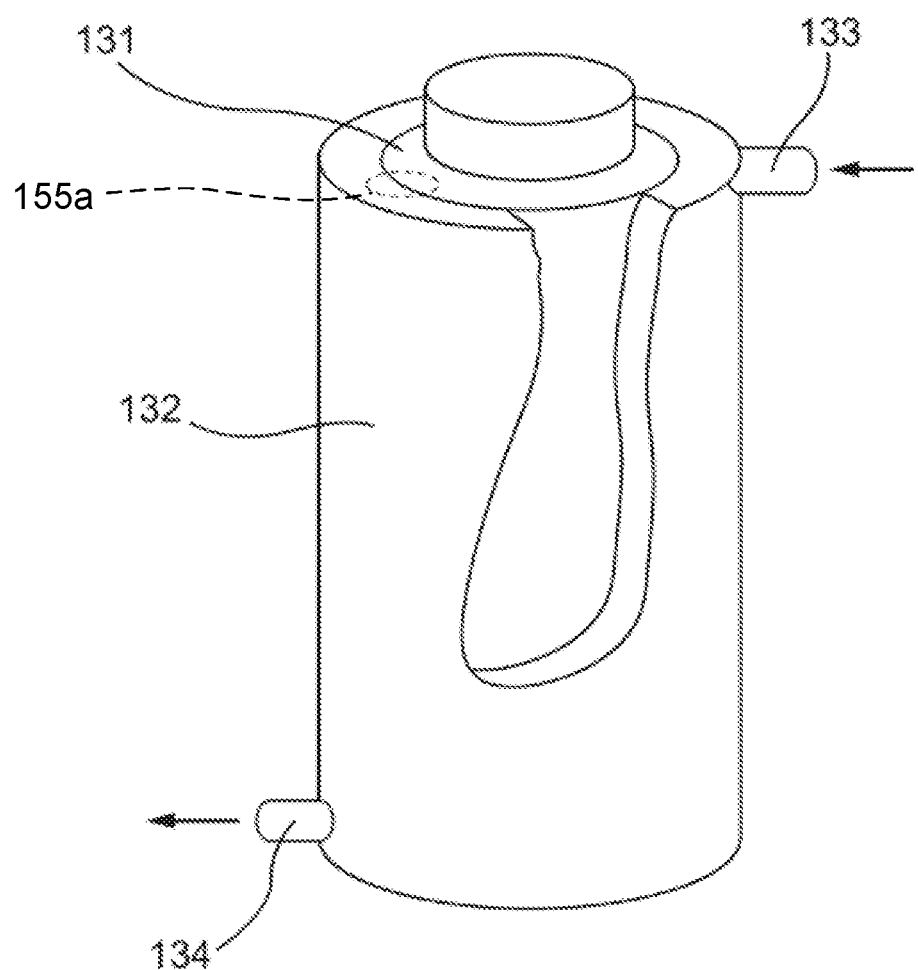
FIG. 13 shows an example system comprising a body and a warming component according to aspects of the present disclosure.

For example, FIG. 13 shows an example body 131 as described herein in communication with a warming component 132. In this example, warming component 132 may comprise a sleeve with a shape sufficient to fit snugly around at least a portion of body 131. In this way, energy from warming component 132 may be transferred from warming component 132 to a lavage fluid contained in body 131 via contacting surfaces of warming component 132 and body 131.

It should be understood that in the example shown in FIG. 13, the contacting surfaces comprise the outer surface of body 131, that is, the surface of body 131 that is in contact with warming component 132. However, it should be understood that the present disclosure is not particularly limited to this arrangement. For example, the contacting surfaces may additionally or alternatively comprise one or more surfaces comprised by one or more channels provided in the body.

Figure 14:
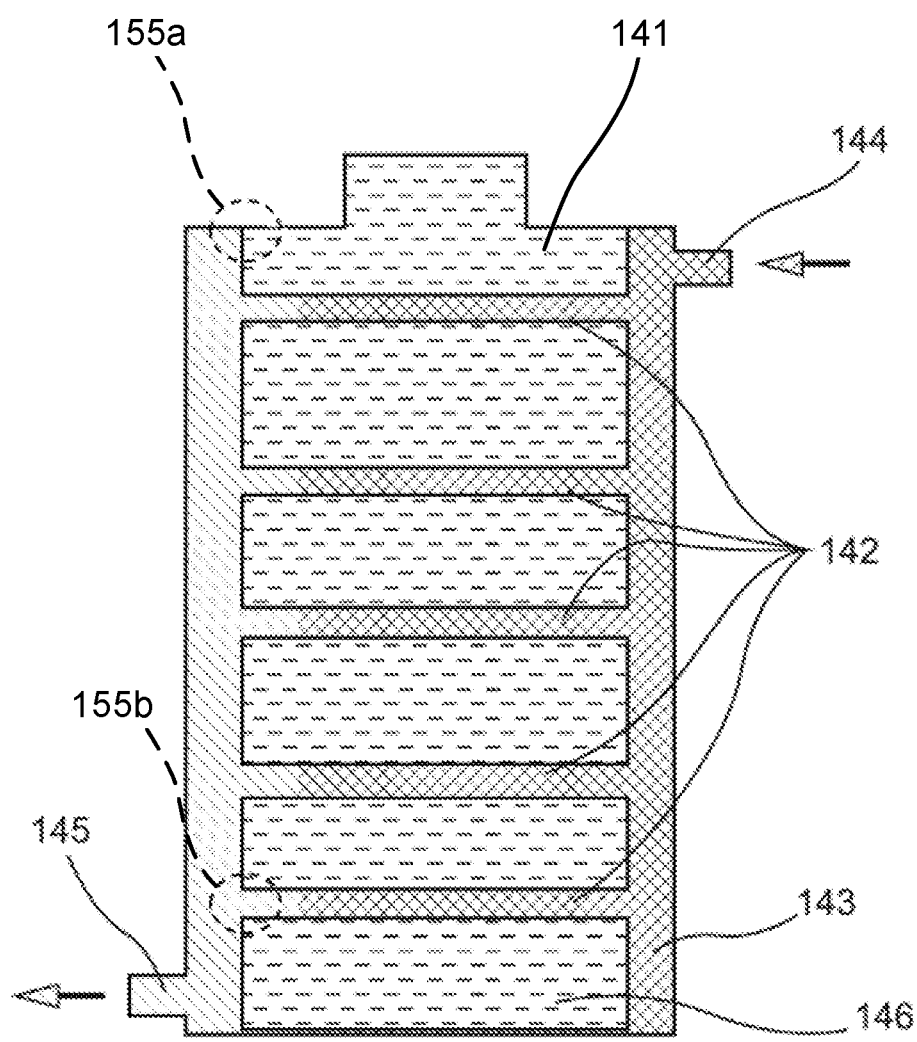
FIG. 14 shows an example system comprising a body and a warming component according to aspects of the present disclosure.

For example, FIG. 14 shows a cutaway view of a body 141 having one or more inner channels 142. It should be understood that each of the one or more inner channels 142 has a surface that increases the total surface of body 141 that contacts a lavage fluid 146 contained therein. In this non-limiting example, a warming component 143 may be configured to contact surfaces of the one or more inner channels 142 in order to transfer energy to a lavage fluid 146 contained in body 141 via contacting surfaces of warming component 143 and body 141. In this way, heat may be evenly distributed to lavage fluid 146 contained in body 141. In addition, warming of lavage fluid 146 contained in body 141 may proceed rapidly at least in part due to the increased surface area of contacting surfaces provided by the one or more inner channels 142.

It should be understood that while the non-limiting example shown in FIG. 14 comprises five evenly distributed inner channels 142 that traverse completely through body 141, a different number, size, and/or shape of inner channels may be selected in order to provide a selected warming distribution and/or rate.

Figure 15:
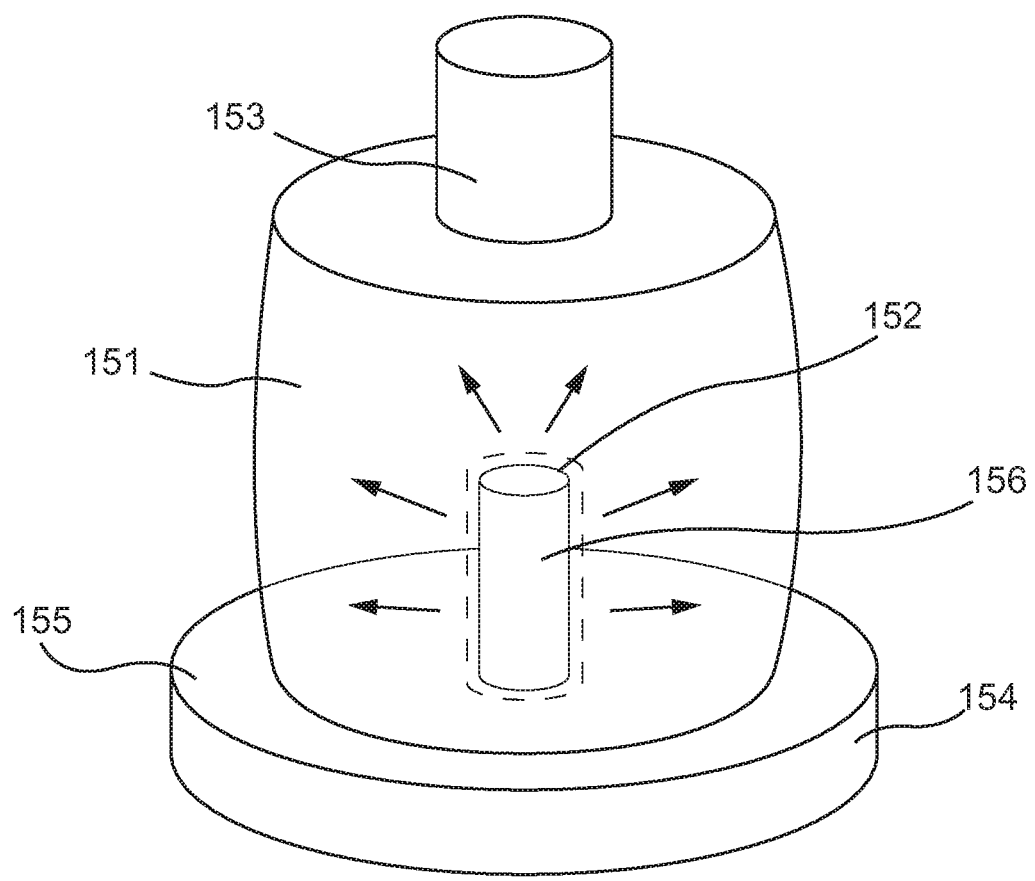
FIG. 15 shows an example system comprising a body and a warming component according to aspects of the present disclosure.

For example, FIG. 15 shows another example of a body 151 having an inner channel 152 as described herein. As shown in FIG. 15, inner channel 152 may be provided relative a side of body 151 that is opposite an aperture 153 as described herein, which may be referred to as a "bottom" of body 151 relative to the ground. In this example, warming component 154 may comprise a base portion 155 configured to interact with the bottom of body 151 and may further comprise a protrusion 156 configured to fit within inner channel 152 of body 151. One or both of base portion 155 and protrusion 156 may be configured to transfer energy as described herein. In this non-limiting example, warming component 154 may additionally provide a support for body 151 such that warming component 154 may warm a lavage fluid contained in body 151 while also providing body 151 in a secure position during the warming process.

In this example, inner channel 152 and protrusion 156 may have a substantially straight shape as shown in FIG. 15. Alternatively, inner channel 152 and/or protrusion 156 may have any shape configured to disconnectably secure body 151 to warming component 154 during warming. For example, inner channel 152 and protrusion 156 may have complimentary curved shapes, such as complimentary corkscrew shapes. Additionally or alternatively, protrusion 156 may comprise one or more threads configured to interact with corresponding threads comprised by inner channel 152 so as to form a screw connection, thereby allowing body 151 to be screwed to warming component 154.

Figure 16:
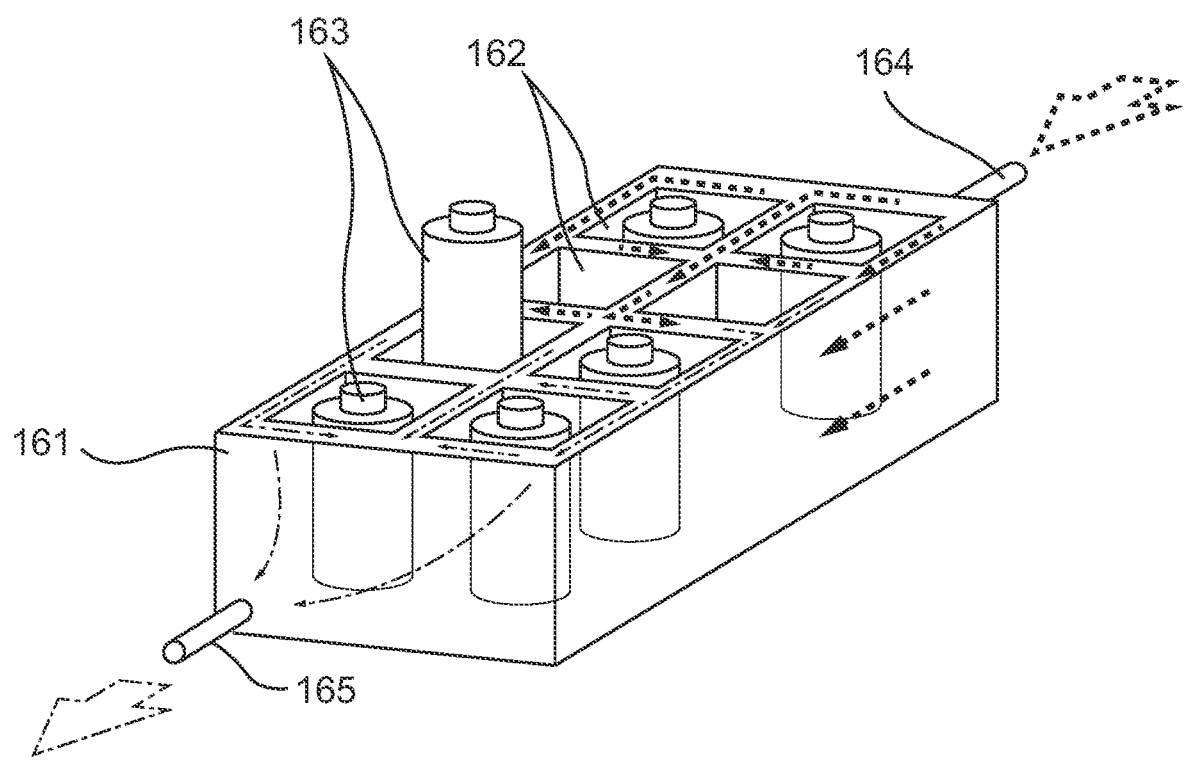
FIG. 16 shows an example system comprising a body and a warming component according to aspects of the present disclosure.

According to some aspects, the warming component may be configured to simultaneously communicate with more than one body. For example, FIG. 16 shows a heating component 161 having more than one body housing 162, each body housing configured to contain a body 163 as described herein. In this way, a single warming component may be used with more than one body as described herein. While not shown, warming component may comprise a lid to at least partially cover one or more of the more than one body housing 162.

The warming component according to the present disclosure is configured to contact a corresponding surface of a body sufficient to transfer energy to a lavage fluid contained in the body, as described herein. It should thus be understood that warming component comprises a source of energy sufficient to warm a lavage fluid to a temperature within an acceptable temperature range and/or to maintain a lavage fluid within an acceptable temperature range as will be described herein.

According to some aspects, the source of energy may comprise a warming material comprised by the warming component. In one non-limiting example, the warming material may comprise a material configured to absorb energy (such as microwave energy) from an external source, such as an external heating chamber. In this example, the warming component may be provided in the external heating chamber for a period of time prior to a lavage process sufficient for the warming component to absorb energy. The warming component may then be provided in contact with a body so as to transfer the absorbed energy to a lavage fluid contained in the body as described herein. In this way, warming the lavage fluid to a temperature within an acceptable temperature range does not require providing a lavage fluid and/or a body into a heating chamber, thereby reducing the risk of unacceptable degradation of the lavage fluid and/or a body material.

Example energy-absorbing materials useful for the warming component include, but are not limited to, one or more organic materials (e.g., rice, buckwheat hulls, corn husks), one or more synthetic materials (e.g., ceramic and/or clay, including ceramic and/or clay beads), and combinations thereof.

Additionally or alternatively, the warming material may comprise an activatable warming material configured to provide heat upon activation. In one non-limiting example, activation may comprise a chemical reaction, such as an exothermic reaction.

In one non-limiting example, the warming material may comprise a first chemical component physically separated from a second chemical component, such as a first chemical component contained in a first cavity and/or a second chemical component contained in a second cavity. In order to activate the warming material, the first chemical component and the second chemical component may be mixed, such as by releasing the first chemical component and/or the second chemical component from the first and/or second cavity, respectively. Upon mixing, the first chemical component may react with the second chemical component to provide heat.

In another non-limiting example, the warming material may comprise a first chemical component separated from an external environment, such as a first chemical component contained in a cavity. In order to activate the warming component, the first chemical component may be contacted with an external environment (e.g., by removal of a cover or tab, and/or by release of the first chemical component from a cavity) such that oxygen contacts the first chemical component. In this example, the first chemical component may react with oxygen to provide heat.

Example activatable warming materials useful according to the present disclosure include, but are not limited to, iron powder and/or activatable mixtures, such as a salt and catalyst mixture. In one non-limiting example, the activatable mixture may comprise water that is supersaturated with a salt (e.g., sodium acetate) to form a solution, the supersaturated solution comprising one or more catalyst particles (e.g., metal particles, glass particles) configured to provide one or more nucleation sites.

Additionally or alternatively, the warming material may comprise a warming fluid. In this example, the warming component may be configured to house the warming fluid.

For example, in the example shown in FIG. 13, warming component 132 may comprise an input 133 through which a warming fluid may be provided within a cavity defined by warming component 132. Warming component 132 may further comprise an output 134 through which a warming fluid may exit. As the warming fluid travels from input 133 to output 134, energy from the warming fluid may be transferred to a lavage fluid contained in body 131 via contacting surfaces of warming component 132 and body 131 as described herein. In this example, warming fluid may be periodically or continually transferred from input 133 to output 143 during a lavage process in order to controllably and rapidly warm a lavage fluid and/or to maintain the temperature of the lavage fluid within an acceptable temperature range.

FIG. 14 shows another example of a warming component 143 having an input 144 and an output 145 as described herein. In this example, a warming fluid may enter warming component 143 via input 144 and travel toward output 145 via the one or more inner channels 142. In this way, a lavage fluid contained in body 141 may be controllably and rapidly heated as described herein.

FIG. 16 shows another example of a warming component 161 having an input 164 and an output 165 as described herein. In this example, a warming fluid may enter warming component 161 via input 164 and travel toward output 165 sufficient to heat bodies 163. In this way, a lavage fluid contained in bodies 163 may be controllably and rapidly heated as described herein.

In one non-limiting example, the warming fluid may comprise heated water alone and/or heated water having one or more adjuncts configured to provide an acceptable specific heat, such as glucose, glycerin, or a combination thereof. Additionally or alternatively, the warming fluid may comprise one or more glycols (e.g., propylene glycol, ethylene glycol), one or more oils (e.g., mineral oil, silicone oil), one or more perfluorocarbons, one or more alcohols (e.g., 1-Octanol), one or more waxes (e.g., paraffin wax), or a combination thereof. It should be understood that as heat from the warming fluid is transferred to the lavage fluid as described herein, the warming fluid may cool. In one example, heated water may enter the warming component via an input as described herein and cooled water may exit the warming component via an output. According to some aspects, the warming fluid may be continually passed through the warming component during at least a portion of a lavage process.

According to some aspects, at least one of the input and the output as described herein may comprise at least one restrictive feature.

In one non-limiting example, the restrictive feature may comprise a one-way valve having a first, closed position that prevents fluid passage therethough and a second, open position that allows fluid passage therethrough. In this example, the input may comprise a one-way valve provided in the first position when subjected to pressure from one direction (i.e., fluid pressure from inside the warming component). The one-way valve may readily move to the second position when subjected to pressure from an opposite different direction (i.e., fluid pressure from outside the warming component). In this way, warming fluid may enter the input as described herein but may be prevented from exiting through the input, thus preventing inadvertent discharge of warming fluid onto a surface (e.g., a surgical site) during a lavage process.

Additionally or alternatively, the restrictive feature may comprise an actuatable valve having a first, closed position and a second, open position, as described herein. In this example, the output may comprise the actuatable valve provided in the first position, wherein the actuatable valve may be selectably actuated to the second position. In this way, warming fluid may exit the output as described herein upon actuation but may be otherwise prevented from exiting through the output, thus preventing inadvertent discharge of warming fluid onto a surface (e.g., a surgical site) during a lavage process.

As described herein, the warming component is configured to warm a lavage fluid to a temperature within an acceptable temperature range and/or to maintain a lavage fluid within an acceptable temperature range. Preferably, the acceptable temperature range is a temperature range suitable for use with a human body during a surgical procedure. For example, the warming component may be configured to warm a lavage fluid to and/or maintain a lavage fluid within a temperature range of between about 32 and 43° C., optionally between about 35 and 37° C., and optionally about 36° C. It should be understood that in order for the warming component to warm a lavage fluid to and/or maintain a lavage fluid within an acceptable temperature range as described herein, the warming component may have a temperature prior to transferring energy to the lavage fluid that is higher than the acceptable temperature range.

For example, the warming component may have a temperature higher than 37° C., optionally between about 37 and 65° C.

According to some aspects, the warming component may be configured to warm a lavage fluid to a temperature within an acceptable temperature range within a certain heating period. According to some aspects, the certain heating period may be no more than about one hour, optionally no more than about 30 minutes, optionally no more than about 25 minutes, optionally no more than about 24 minutes, optionally no more than about 23 minutes, optionally no more than about 22 minutes, optionally no more than about 21 minutes, optionally no more than about 20 minutes, optionally no more than about 19 minutes, optionally no more than about 18 minutes, optionally no more than about 17 minutes, optionally no more than about 16 minutes, optionally no more than about 15 minutes, optionally no more than about 14 minutes, optionally no more than about 13 minutes, optionally no more than about 12 minutes, optionally no more than about 11 minutes, optionally no more than about 10 minutes, optionally no more than about 9 minutes, optionally no more than about 8 minutes, optionally no more than about 7 minutes, optionally no more than about 6 minutes, optionally no more than about 5 minutes, optionally no more than about 4 minutes, optionally no more than about 3 minutes, optionally no more than about 2 minutes, optionally no more than about 1 minute, optionally no more than about 45 seconds, and optionally no more than about 30 seconds.

According to some aspects, the system according to the present disclosure comprises a reusable warming component configured for more than one warming process, particularly more than one warming process with more than one body.

According to some aspects, the device or system according to the present disclosure may also comprise a temperature indicator, e.g., as indicated by reference numbers 155*a* in FIGS. 13 and 155*a* and 155*b* in FIG. 14, configured to indicate that a certain temperature or temperature range of a lavage fluid has been attained. The temperature indicator may be an integral part of one or more components of the device or system as described herein, such as an integral part of a body and/or a warming component. Additionally or alternatively, the temperature indicator may be a disparate component of the system configured to communicate with a body as described herein. The temperature indicator may be selectively communicatable with the body, for example, an attachment that may be provided in selective communication with the body during lavage fluid warming.

According to some aspects, the temperature indicator may indicate a certain temperature or temperature range of a lavage fluid contained in a body via a signal. The certain temperature or temperature range may be a temperature or temperature range that is within an acceptable temperature range as described herein, wherein the signal is not present when the lavage fluid has a temperature that is outside of the acceptable temperature range. In this way, the temperature indicator may prevent the use of a lavage fluid having a temperature that is too low and/or too high for use in a lavage process.

In one non-limiting example, the signal may be a change in color. In this example, the temperature indicator may comprise a temperature-sensitive material having a first color (wherein the first color may be a colorless) when contacted with a temperature that is below a selected temperature or temperature range, such as a temperature below an acceptable temperature range as described herein. The temperature-sensitive material may have a second color (wherein the second color may be colorless) when contacted with a temperature that is within a selected a temperature range, such as an acceptable temperature range as described herein. Optionally, the temperature-sensitive material may have a third color (wherein the third color may be colorless) when contacted with a temperature that is above a selected temperature or temperature range, such as a temperature above an acceptable temperature range as described herein. According to some aspects, the first color and the third color are different from the second color. Optionally, the first color may be different from the third color.

According to some aspects, the temperature-sensitive material may be in direct contact with a lavage fluid. For example, a body as described herein may be formed at least in part from a temperature-sensitive material such that the temperature-sensitive material contacts a lavage fluid contained in the body. Additionally or alternatively, the temperature-sensitive material may not be in direct contact with a lavage fluid. For example, the temperature-sensitive material may be contact with an exterior portion of a body sufficient to sense a temperature of a lavage fluid contained in the body.

Example temperature-sensitive materials useful according to the present disclosure include, but are not limited to, one or more thermochromic paints (e.g., liquid crystals, leuco dyes, paints comprising one or more inorganic compounds), one or more thermochromic pigments, one or more inks, or a combination thereof.

Additionally or alternatively, the signal may comprise a positional change of fluid comprised by the temperature indicator. For example, the temperature indicator may comprise a conduit containing a fluid, wherein the fluid has a first position when contacted with a temperature that is below a selected temperature or temperature range, such as a temperature below an acceptable temperature range as described herein. The fluid may have a second position when contacted with a temperature that is within a selected a temperature range, such as an acceptable temperature range as described herein. For example, the second position may comprise a rise in the fluid within the conduit. Optionally, the temperature-sensitive material may have a third position when contacted with a temperature that is above a selected temperature or temperature range, such as a temperature above an acceptable temperature range as described herein. According to some aspects, the first position and the third position are different from the second position. Optionally, the first position may be different from the third position.

According to some aspects, the conduit may comprise a fluid path along which the fluid may advance via capillary action. As used herein, the term "capillary action" refers to the action of a fluid flowing into and through a space without the assistance of and/or in opposition to external forces such as gravity. In one non-limiting example, the conduit may have a length to diameter ratio sufficient to achieve capillary action. The temperature indicator may comprise one or more conduit groups, wherein each of the one or more conduit groups comprises one, two, three, or more conduits in order to provide acceptable visibility to a user. The fluid contained in the one or more conduits may comprise any fluid configured to move via capillary action as described herein, such as water, an alcohol, and/or any liquid with a sufficient coefficient of thermal expansion so as to move via capillary action. According to some aspects, the fluid may comprise a tinting agent as described herein. It should be understood that the fluid comprised by the temperature indicator as described herein may remain in a liquid state when contacted with heat provided by a warming component as described herein.

According to some aspects, the conduit may not be in direct contact with a lavage fluid, thus eliminating the requirement for the conduit to be sterile. For example, the conduit may be in contact with an exterior portion of a body sufficient to sense a temperature of a lavage fluid contained in the body. Additionally or alternatively, the body may comprise one or more interior channels as described herein, wherein the one or more interior channels are configured to communicate with a portion of the temperature indicator, such as the conduit or a probe configured to communicate with the conduit. In this example, the conduit or probe may be inserted into the channel sufficient to sense the temperature of a lavage fluid contained in the body without requiring the conduit or probe to be in direct contact with the lavage fluid.

Additionally or alternatively, the signal may comprise the appearance of text, a symbol, or other observable cue. Additionally or alternatively, the signal may comprise an audible signal, such as an alarm. According to the some aspects, the temperature indicator may comprise a device, such as a thermocouple, that is communicable with an external device, such as an external electronic device. The external electronic device may be configured to provide a signal as described herein. In one non-limiting example, the thermocouple may be hardwired to the external electronic device. Additionally or alternatively, the thermocouple may be configured to communicate with the external electronic device via wireless technology, such as via Bluetooth® technology.

According to some aspects, the devices and/or systems according to the present disclosure may comprise a component configured to shake, rotate, vibrate, or otherwise move the body sufficient to provide a more even distribution of warmed lavage fluid within the body. For example, the component may comprise an apparatus configured to shake, rotate, vibrate, or otherwise move the body with or without a warming component as described herein during and/or after a warming process. In this way, warmed fluid within the body may be more evenly distributed therethrough, thus providing a more rapid and efficient warming process.

The body according to the present disclosure may comprise a connection portion configured to selectively place the body in fluid communication with an applicator member. As used herein, the term "connection portion" refers to a portion of the body configured to provide a secure connection between the body and an application member such that fluid (e.g., an antiseptic solution) may be controllably dispensed from the body to the application member.

In one example, the connection portion is configured to fix the body and the application member such that a first aperture comprised by the body is aligned with a second aperture comprised by the application member sufficient to provide fluid communication between the body and application member. The connection portion may comprise any connection types known in the art useful according to the present disclosure.

Figure 3:
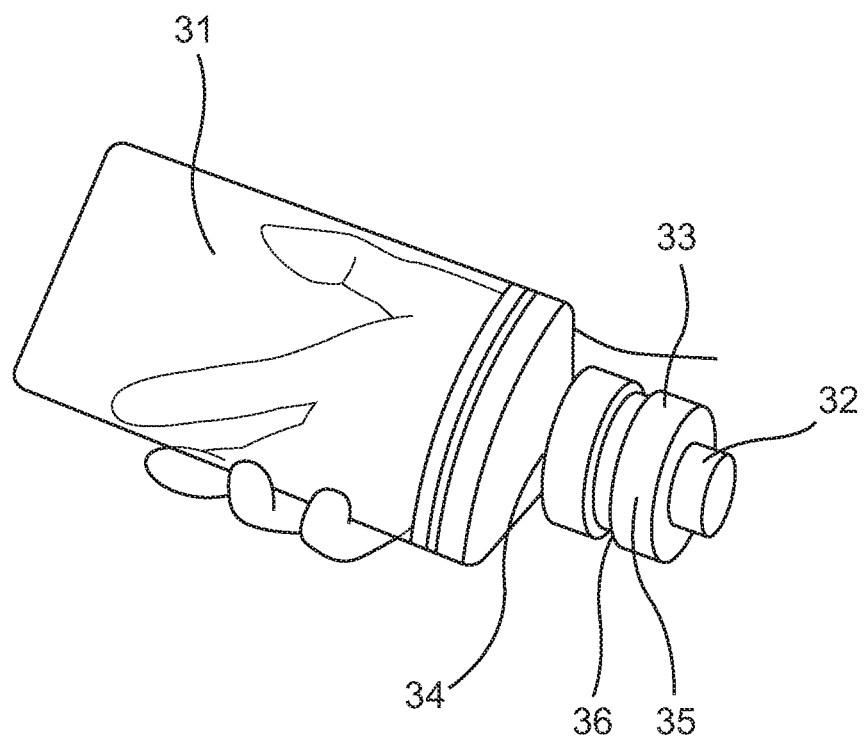
FIG. 3 shows an example of a body's connection portion according to aspects of the present disclosure.

FIG. 3 shows an example of a connection portion 33 configured to connect a body 31 with an application member 32. In this example, connection portion 33 comprises protrusions configured to interact with corresponding protrusions comprised by the application member so as to form a screw connection, thereby allowing body 31 to be screwed to application member 32. It should be understood that in this example, screwing body 31 to application member 32 via connection portion 33 will align an aperture 34 of body 31 with an aperture 35 of application member 32 so as to provide fluid communication between body 31 and application member 32 when connected.

According to some aspects, the body may be provided with a removable lid, for example, a cap configured to interact with the connection portion of the body in place of the application member. It should be understood that the lid may prevent fluid discharge from the body, for example, during storage or transportation of the body.

According to some aspects, the connection portion may be provided with a fluid metering device, for example, a valve. The fluid metering device may be provided in communication with the body aperture (e.g., provided in the body aperture) sufficient to affect fluid flow from the body.

The present disclosure is also directed to a system comprising a body as described herein and one or more application members. The one or more application members may each be configured to apply a lavage fluid to a surface sufficient for a lavage process.

According to some aspects, the body may comprise a connection portion configured to interact with two or more different application members such that the system is adapted for interchanging application members. For illustrative purposes, taking the example shown in FIG. 3, the system may comprise a body 31 having a connection portion 33 as shown. The system may further comprise one or more application members each having a connection portion 36 with substantially the same size and shape such that each of the one or more application members may be interchangeably connected with body 31. In this way, a user may select from two or more application members based on lavage process preferences and requirements without requiring multiple body types. The system according to the present disclosure therefore beneficially allows a user to select from a variety of different application members, each of which may provide a unique fluid flow rate, fluid flow pattern, and/or fluid flow force, as will be described in more detail herein.

Figure 5:
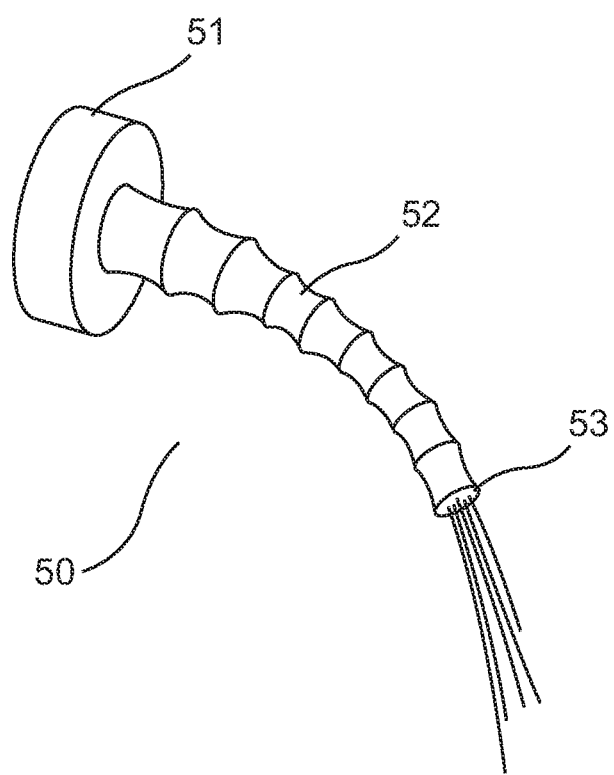
FIG. 5 shows an example application member according to aspects of the present disclosure.

FIG. 5 shows one example application member 50 according to the present disclosure. As shown in FIG. 5, application member 50 may comprise a connection portion 51 and a discharge portion 52. Connection portion 51 may be configured to connect the application member 50 with a body as described herein. Discharge portion 52 may comprise one or more discharge apertures 53 configured to dispense a fluid (e.g., an antiseptic solution as described herein) onto a surface, such as a surgical site during a lavage process.

In the example shown in FIG. 5, discharge portion 52 may comprise a semi-flexible conduit such that the shape and/or orientation of the conduit is adjustable. In this way, the angle and/or direction of fluid discharge may be adjusted before and/or during a lavage process. As used herein, the term "semi-flexible" refers to the ability to bend or compress in addition to the ability to maintain shape when subjected to operating pressure, such as the pressure from fluid flow and/or the handling by a user. According to some aspects, the degree of flexibility of a semi-flexible component may depend at least in part on the application member material, the shape of the discharge portion, the length of the discharge portion, or a combination thereof. It should be understood that application member 50 as shown in FIG. 5 advantageously provides control of the flow path of a dispensed fluid such that a user may direct a fluid (e.g., an antiseptic solution) toward irregularly shaped and/or difficult to reach surfaces, such as irregularly shaped and/or difficult to reach surgical sites.

Figure 6:
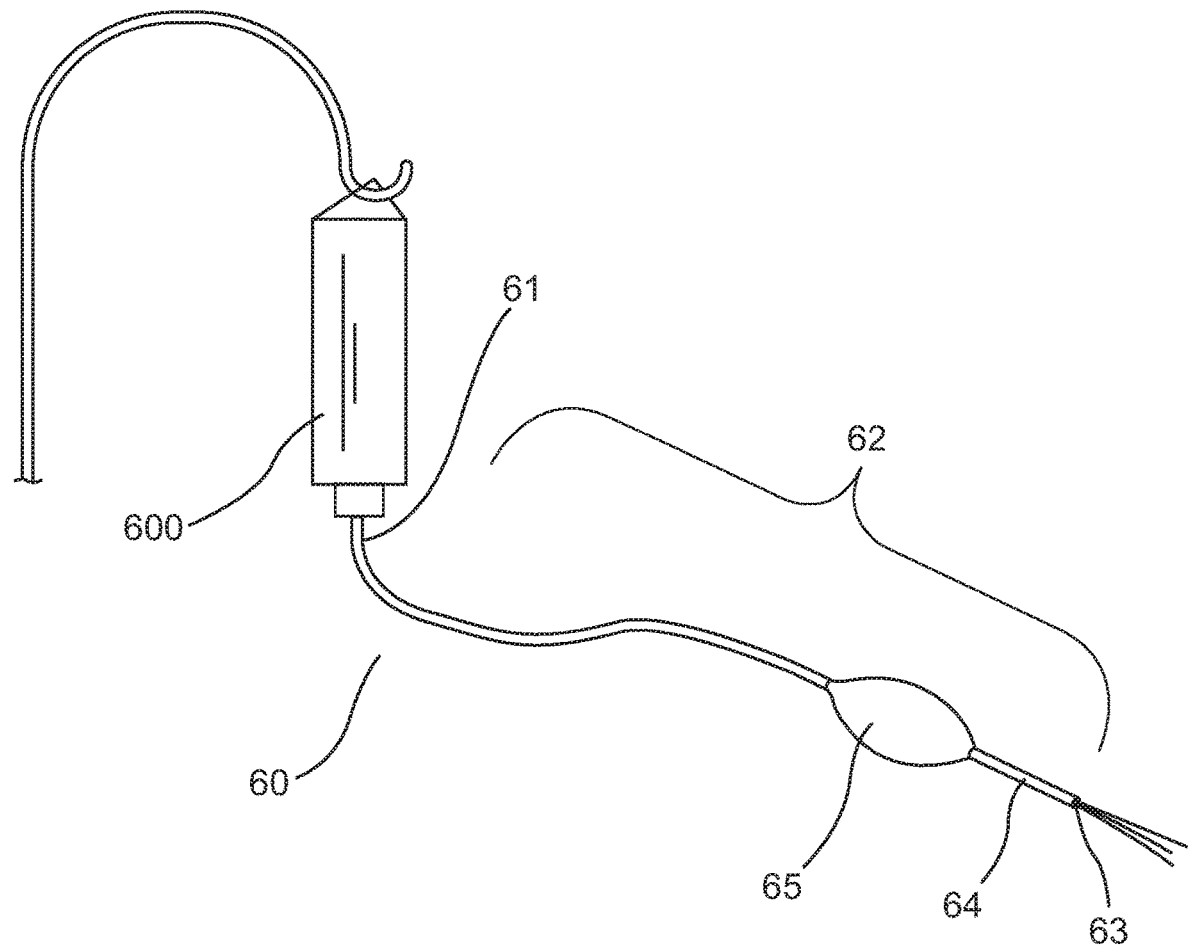
FIG. 6 shows an example system according to aspects of the present disclosure.

FIG. 6 shows another example application member 60 according to the present disclosure. As shown in FIG. 6, the application member 60 may comprise a connection portion 61 and a discharge portion 62. Connection portion 61 may be configured to connect application member 60 with body 600 as described herein. Discharge portion 62 may comprise one or more discharge apertures 63 configured to dispense a fluid (e.g., an antiseptic solution) onto a surface, such as a surgical site during a lavage process. It should be understood that discharge portion 62 may comprise a conduit 64 that may be a semi-flexible conduit as described in relation to FIG. 5, a flexible conduit, or a rigid conduit.

Figure 7A:
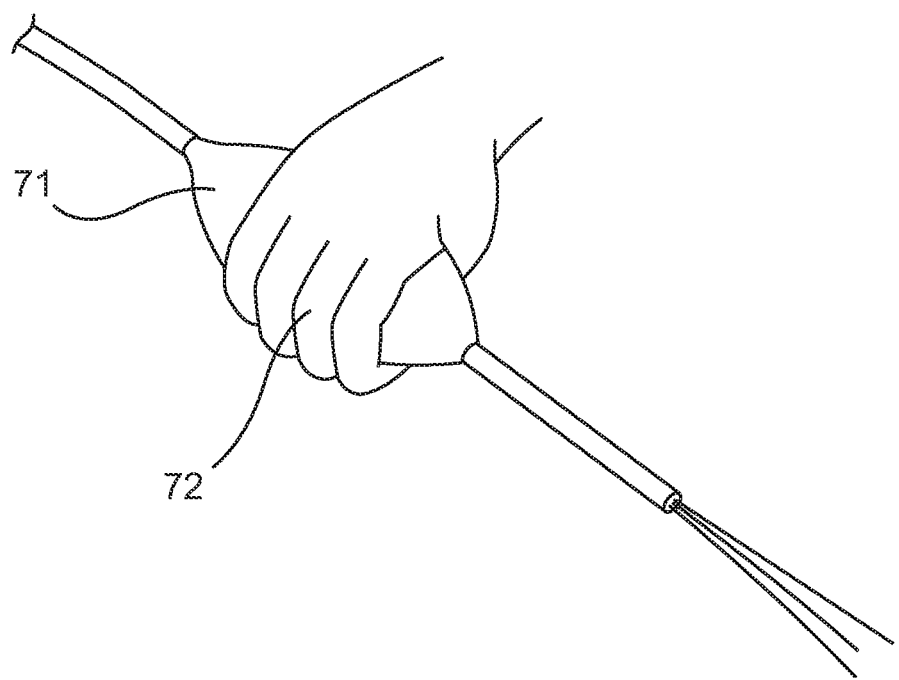
FIG. 7A shows an example dispensing aid according to aspects of the present disclosure.
Figure 7B:
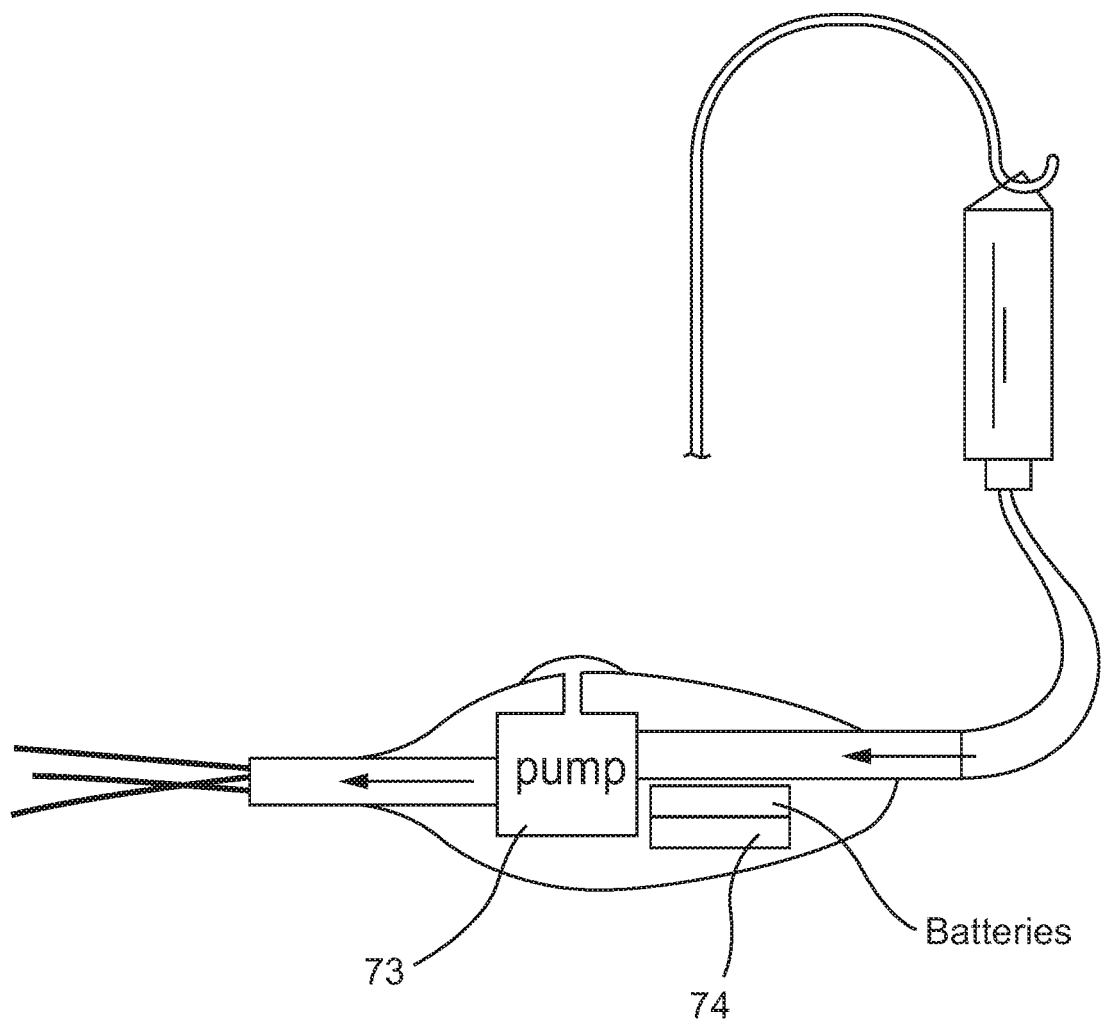
FIG. 7B shows an example dispensing aid according to aspects of the present disclosure.

As shown in FIG. 6, application member 60 may further comprise a dispensing aid 65 as described herein, such as a pump. Dispensing aid may be a mechanical pump, for example, as shown in FIG. 7A. FIG. 7A shows a hand pump 71 that moves fluid upon compression by a user's hand 72. Additionally or alternatively, dispensing aid may be a motorized pump as shown in FIG. 7B. FIG. 7B shows a motorized pump 73 that moves fluid via electrical energy produced by, for example, batteries 74.

It should be understood that application member 60 having dispensing aid 65 as described herein may dispense a lavage fluid (e.g., an antiseptic solution) from body 600 upon actuation of dispensing aid 65 (e.g., actuation of a pump as described herein). Additionally or alternatively, dispensing aid 65 may function to dispense fluid from body 600 in conjunction with the force of gravity. For example, FIG. 6 shows an example body 600 similar to the body shown in FIG. 2A, that is, a body configured such that at least a portion of the lavage fluid contained therein is dispensed by the force of gravity when provided in a certain orientation. It should be understood that the dispensing aid will advantageously allow a user to control the fluid flow force, the fluid flow rate, and/or the fluid flow pattern (e.g., pulsed or constant) of the dispensed lavage fluid.

While the examples shown in FIGS. 5 and 6 show discharge portions having one discharge aperture, it should be understood that the discharge portion may comprise two, three, four, or more discharge apertures. Each of the discharge apertures may be the same size as or a different size from one or more of the other discharge apertures. Additionally or alternatively, each of the discharge apertures may have the same shape as or a different shape from one or more of the other discharge apertures. The shape and/or size of the one or more discharge apertures may be selected to provide a certain fluid flow force, fluid flow rate, and/or fluid flow pattern. According to some aspects, the shape and/or size of the one or more discharge apertures may be adjustable such that the fluid flow force, fluid flow rate, and/or fluid flow pattern of a dispensed fluid may be adjustable.

Figure 8:
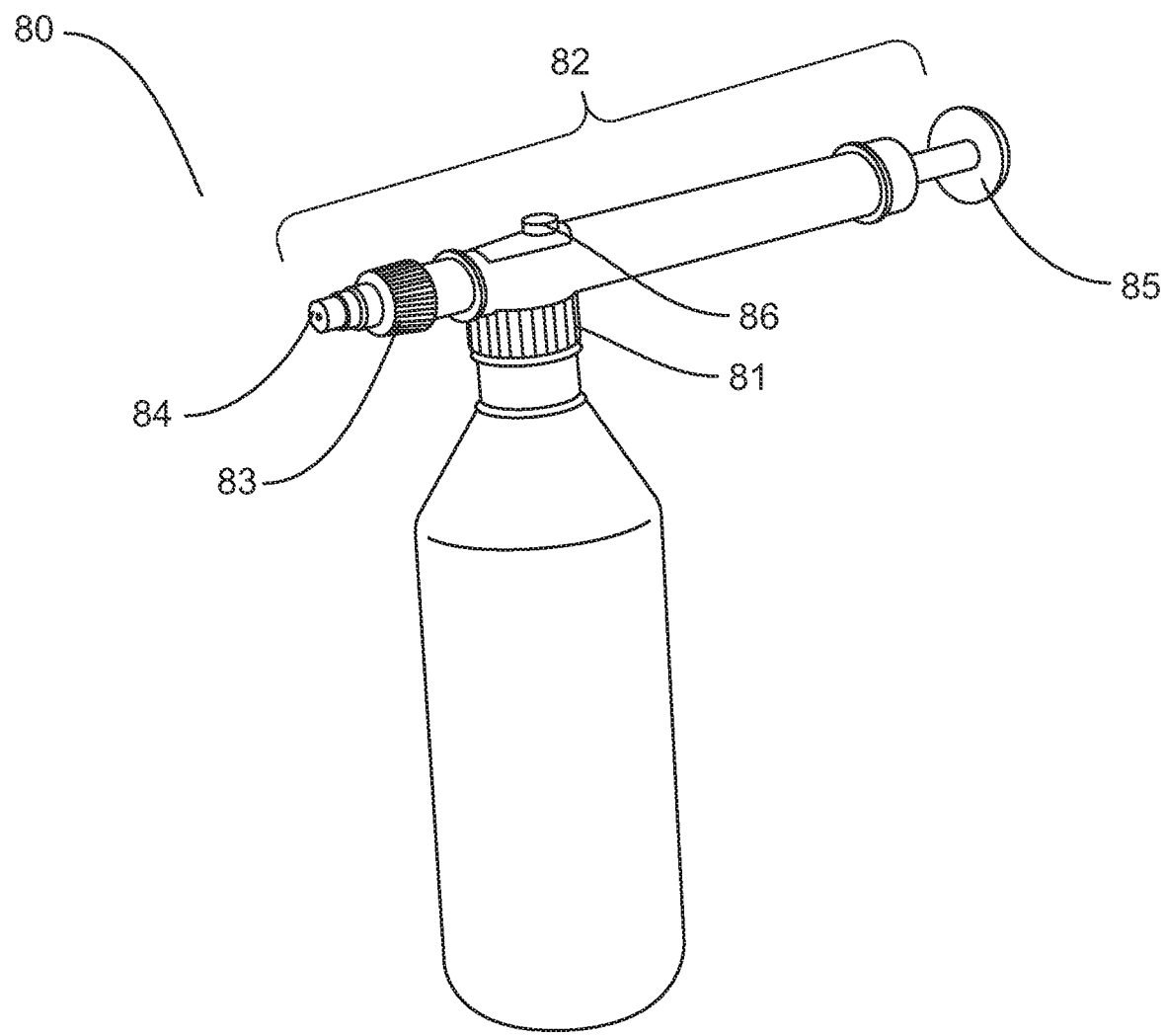
FIG. 8 shows an example system according to aspects of the present disclosure.

According to some aspects, the one or more discharge apertures may be provided in a nozzle portion of the discharge portion of an application member. For example, FIG. 8 shows a body 800 in fluid communication with an application member 80 having a connection portion 81 and a discharge portion 82 as described herein. As shown in FIG. 8, discharge portion 82 may comprise a nozzle 83 having one or more discharge apertures 84 as described herein. It should be understood that nozzle 83 may be removable and replaceable, thereby allowing the same application member 80 to interchangeably comprise at least two different nozzles 83. The system according to the present disclosure may thus comprise at least one application member and two or more interchangeable nozzles as described herein.

In the example shown in FIG. 8, application member 80 may further comprise a dispensing aid comprising a pump shaft 85 and an actuator 86, such as a button. In this example, nozzle 83 may be adapted to provide a mist of fluid in conjunction with pump shaft 85 upon actuation of actuator 86 by any mechanism known in the art. It should be understood that nozzle 83 may additionally or alternatively be configured to provide a stream of fluid, a spray of fluid, or a combination thereof.

Figure 9:
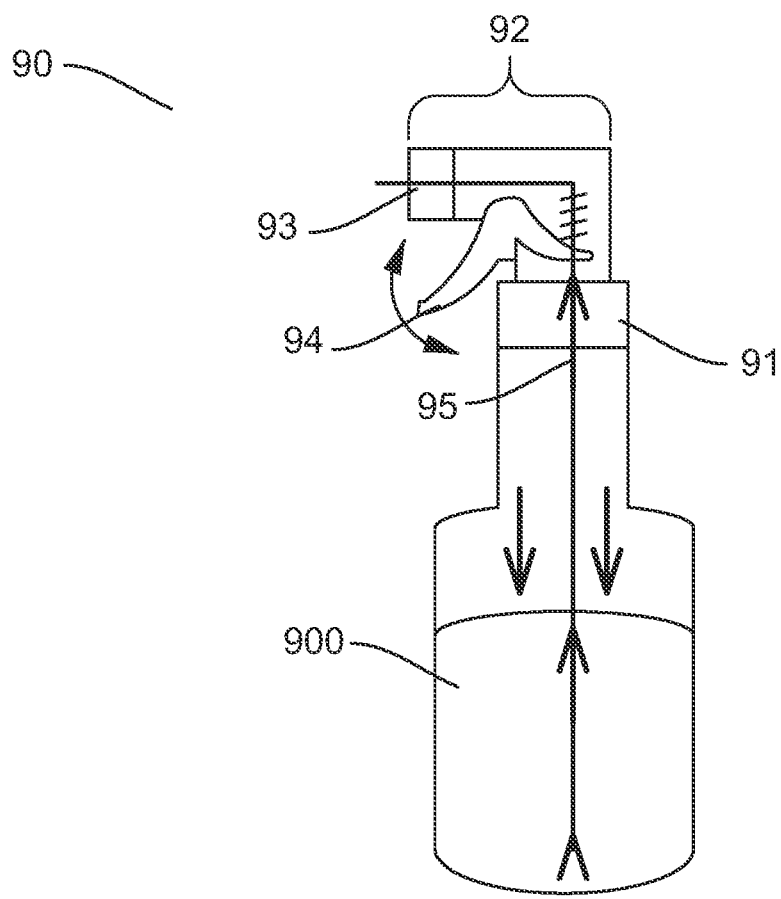
FIG. 9 shows an example system according to aspects of the present disclosure.

FIG. 9 shows another example of a system according to the present disclosure. As shown in FIG. 9, application member 90 may comprise a connection portion 91 and a discharge portion 92 as described herein. Discharge portion may comprise a nozzle 93 and an actuator 94, such as a trigger. In this example, application member 90 may further comprise a conduit 95 in fluid communication with a fluid contained in body 900 as described herein. In this example, body 900 may be pressurized. Upon actuation of actuator 94 (such as compressing the trigger), pressure in conduit 95 may drop below the pressure of body 900, thus forcing fluid from body 900 unto application member 90. Nozzle 93 may be configured to provide, for example, a fluid stream, a fluid mist, a fluid spray, or a combination thereof.

Figure 10:
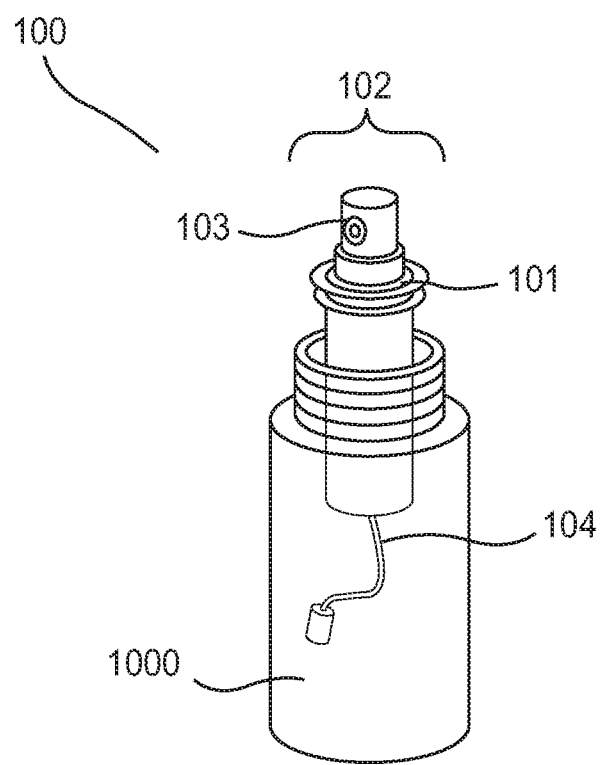
FIG. 10 shows an example system according to aspects of the present disclosure.

FIG. 10 shows another example of a system according to the present disclosure. As shown in FIG. 10, application member 100 may comprise a connection portion 101 and a discharge portion 102 as described herein. Discharge portion may comprise a nozzle 103. In this example, nozzle 103 may also function as an actuator, for example, by pressing nozzle 103 toward body 1000. Application member 100 may further comprise a conduit 104 in fluid communication with a fluid contained in body 1000. As described in relation to FIG. 9, body 1000 may be pressurized. Upon actuation of nozzle 103, pressure in conduit 104 may drop below the pressure of body 1000, thus forcing fluid from body 1000 unto application member 100, as described in relation to FIG. 9.

Figure 11:
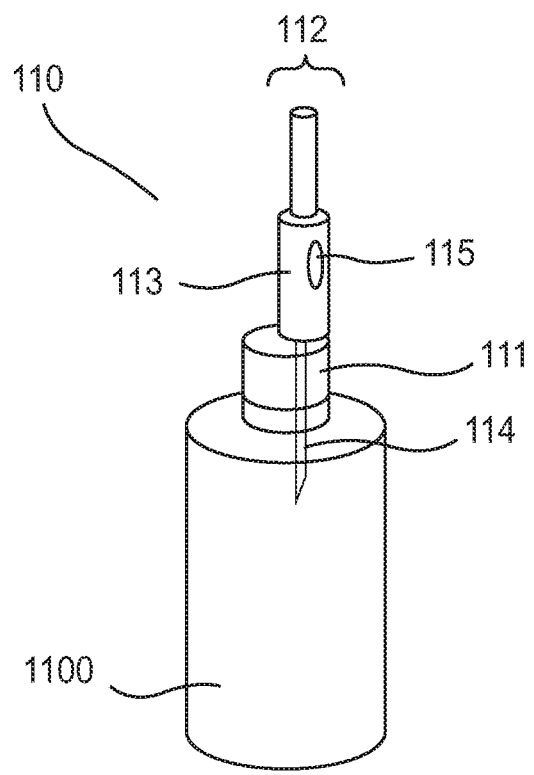
FIG. 11 shows an example system according to aspects of the present disclosure.

FIG. 11 shows another example system according to the present disclosure, including an application member 110, connection portion 111, discharge portion 112 including nozzle 113, and conduit 114, similar to the example shown in FIG. 10. FIG. 11 shows that nozzle 113 may further comprise an actuator 115, such as a button. As described in relation to FIGS. 9 and 10, body 1100 may be pressurized such that, upon actuation of actuator 115 (i.e., by pressing the button), pressure in conduit 114 may drop below the pressure of body 1100, thus forcing fluid from body 1100 into application member 110.

Figure 12:
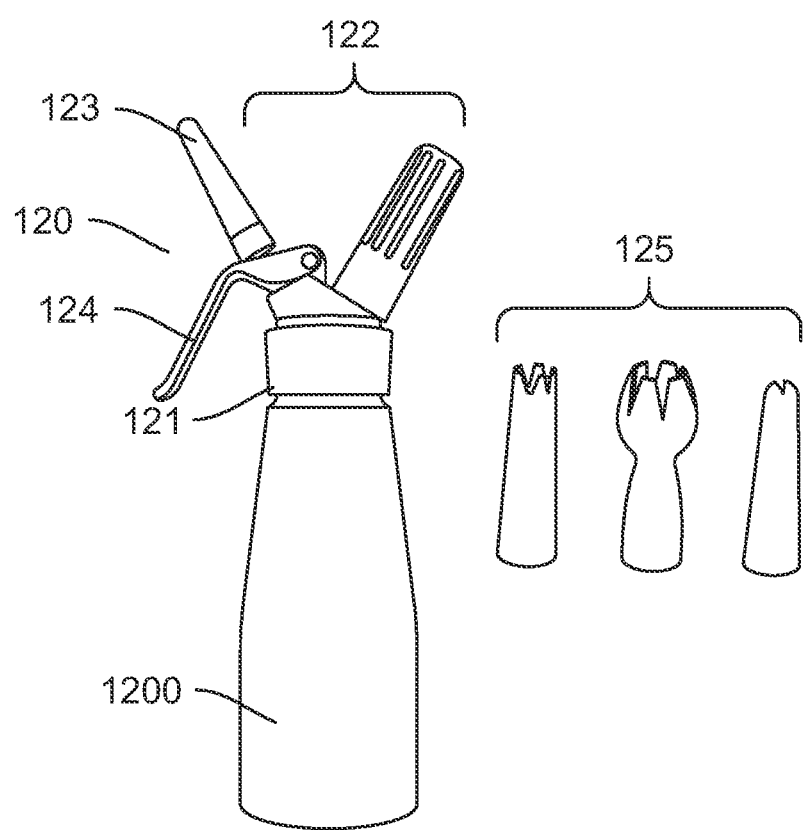
FIG. 12 shows an example system with more than one nozzle according to aspects of the present disclosure.

FIG. 12 shows another example of a system according to the present disclosure. As shown in FIG. 12, application member 120 may comprise a connection portion 121 and a discharge portion 122 as described herein. Discharge portion may comprise a first nozzle 123 and an actuator 124. As described in relation to FIGS. 9, 10, and 11, body 1200 may be pressurized. Additionally or alternatively, the system may comprise a cartridge containing a propellant (not shown) configured to provide an aerosol as known in the art. The propellant may be any propellant acceptable for medical use according to the present disclosure, including, but not limited to, carbon dioxide, nitrous oxide, nitrogen, helium, argon, air, and any combination thereof. As used herein, the term "air" refers to the natural atmosphere of the Earth.

The example system shown in FIG. 12 also shows a plurality of interchangeable nozzles 125 as described herein. It should be understood that each of the plurality of interchangeable nozzles 125 is configured to be interchangeable with nozzle 123, thus providing a single application member 120 and body 1200 configured to dispense a fluid to a surface via a variety of nozzles so as to provide a variety of different, selectable fluid flow rates, fluid flow patterns, and/or fluid flow forces, as described herein. It should be understood that the systems described herein may comprise at least a body configured to be in fluid communication with one or more different application members, each of the one or more different applications members having at least one discharge aperture, wherein the at least one discharge aperture is optionally comprised by a removable and replaceable nozzle, as described herein. It should be understood that the systems as described herein may thus be configured to deliver a lavage fluid to a surface via one or more different, selectable fluid flow rates, fluid flow patterns, and/or fluid flow forces, as described herein.

For example, the system may comprise at least two different application members and/or at least two different nozzles as described herein, wherein each of the at least two different application members and/or at least two different nozzles are configured to provide a unique fluid flow rate, fluid flow pattern, and/or fluid flow force. According to some aspects, a single application member and/or a single nozzle may be configured to provide at least two unique fluid flow rates, fluid flow patterns, and/or fluid flow forces, such as by providing one or more discharge apertures with adjustable shapes and/or sizes, as described herein.

According to some aspects, the system may be configured to provide an acceptable fluid flow rate for a lavage process. As used herein, the term "fluid flow rate" refers to the rate at which a fluid is applied to a surface, such as to a human subject during a lavage process. The fluid flow rate may depend at least partially on the delivery mechanism (e.g., compressing the body, orientating the body, utilizing a dispensing aid, or a combination thereof, as described herein) and/or the properties of the application member and/or nozzle as described herein. According to some aspects, a fluid flow rate may be related to a fluid flow force. For example, an increased fluid flow rate may correspond with an increased fluid flow force, and vice versa. The system according to the present disclosure may be configured to provide at least two different, selectable fluid flow rates, optionally at least three, optionally at least four, and optionally at least five.

According to some aspects, the system may be configured to provide an acceptable fluid flow force for a lavage process. As used herein, the term "fluid flow force" refers to the force of a fluid acting on a surface, such as on a human subject during a lavage process. An acceptable fluid flow force may be determined based on the lavage process requirements. Example fluid flow forces useful according to the present disclosure include, but are not limited to, between about 10 and 50 g, and optionally between about 15 and 45 g. According to some aspects, the fluid flow force may be about 15 g. According to some aspects, the fluid flow force may be between about 30 and 45 g. Other example fluid flow forces useful according to the present disclosure include, but are not limited to, between about 1 and 15 psi (referred to herein as "low pressure") and between about 35 and 70 psi (referred to herein as "high pressure").

It should be understood that the fluid flow force provided by the systems as described herein may depend at least partially on the delivery mechanism and/or the properties of the application member and/or nozzle as described herein. The system according to the present disclosure may be configured to provide at least two different, selectable fluid flow forces, optionally at least three, optionally at least four, and optionally at least five. It should be understood that each of the selectable fluid flow forces may correspond with, for example, a specific delivery mechanism, a specific application member, a specific nozzle, or a combination thereof, as described herein. For example, one or more selectable flow forces may correspond with an application member having an actuator as described herein, such as a trigger, wherein each of the one or more selectable flow forces may correspond with a degree of trigger compression. In another example, one or more selectable flow forces may correspond with a nozzle having one or more discharge apertures, wherein each of the one or more selectable flow forces may correspond with the shape and/or size of the one or more discharge apertures.

According to some aspects, the system is configured to provide an acceptable fluid flow pattern for a lavage process. As used herein, the term "fluid flow pattern" refers to the pattern with which a fluid is dispensed from a device and/or applied to a surface, such as to a human subject during a lavage process. In some non-limiting examples, the fluid flow pattern may comprise a fluid mist (i.e., a suspension of finely divided fluid in a gas), a fluid stream (i.e., a steady succession of fluid), a fluid spray (i.e., finely divided fluid), or a combination thereof. The fluid flow pattern may be constant (e.g., fluid continually dispensed from a device and/or applied to a surface) or pulsed (e.g., the fluid intermittently dispensed from a device and/or applied to a surface).

A fluid flow pattern may additionally or alternatively refer to the angle at which a fluid flow path is dispensed from a device and/or applied to a surface. For example, a fluid flow path may have a fluid flow pattern that is about perpendicular to a longitudinal axis of a body as described herein.

Additionally or alternatively, a fluid flow pattern may refer to the geometric shape of a fluid path. It should be understood that the geometric shape of a fluid path refers to a shape defined by the cross-sectional view of a fluid flow path in any of the x-direction, y-direction, and z-direction.

It should be understood that the fluid flow pattern may depend at least in part on the delivery mechanism and/or the application member and/or nozzle as described herein. The system according to the present disclosure may be configured to provide at least two different, selectable fluid flow patterns, optionally at least three, optionally at least four, and optionally at least five. For example, one or more selectable flow patterns may correspond with a dispensing aid such as a pump, wherein the pump may be configured to provide a constant flow of fluid from the body and/or to provide a pulsed flow of fluid from the body. In another example, one or more selectable flow patterns may correspond with the application member's discharge portion, such as a discharge portion comprising a semi-flexible conduit as described herein. In this example, the one or more selectable flow patterns may comprise one or more fluid delivery angles corresponding with the shape and/or orientation of the semi-flexible conduit as described herein.

According to some aspects, one or more components of the system described herein may be provided in sterile packaging. As used herein, the term "sterile packaging" refers to packaging that provides a sterile environment so as to maintain sterility of a contained sterile product. Example sterile packaging includes, but is not limited to, sterile buster packaging, sterile safe-edge trays, sterile surgical trays, sterile customized thermoforms, and combinations thereof. It should be understood that one or more components of the system may be provided in the same sterile packaging and/or separate sterile packaging from at least one other component of the system. For example, a first component of the system may be contained in a first sterile packaging and a second component of the system may be contained in a second sterile packaging. In one non-limiting example, the system may comprise a body contained in a first sterile packaging and an application member contained in a second sterile packaging. In another non-limiting example, the system may comprise a body contained in a first sterile packaging, an application member contained in a second sterile packaging, and/or a warming component contained in a third sterile packaging. It should be understood that providing one or more components of the system in different sterile packaging allows for the removal of each component of the system immediately prior to its use, thus preventing one or more components from prolonged exposure to an unsterile environment. In this way, a fully assembled sterile presentation of the system may be achieved.

The present disclosure is also directed to methods of using the devices and systems described herein. For example, the method may comprise providing a body containing a lavage fluid, wherein the body comprises a connection portion. The method may comprise placing the body in fluid communication with an application member and dispensing the lavage fluid as described herein sufficient to perform a lavage process.

In another example, the method may comprise providing a body containing a lavage fluid, the body being in communication with a warming component as described herein. The method may comprise warming the lavage fluid contained in the body to a temperature within an acceptable temperature range via contacting surfaces of the warming component and the body. The method may also optionally comprise observing a temperature indicator for a signal as described herein, wherein the signal indicates a certain temperature or temperature range of the lavage fluid contained in the body. The method may further comprise dispensing the lavage fluid sufficient to perform a lavage process.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

The word "about" is used herein to mean within ±5% of the stated value, optionally within ±4%, optionally within ±3%, optionally within ±2%, optionally within ±1%, optionally within ±0.5%, optionally within ±0.1%, and optionally within ±0.01%.

What is claimed is:

1. A system for applying a lavage fluid to a surface, the system comprising:
   a body configured to house a lavage fluid;
   an application member in fluid communication with the body, wherein the application member is configured to dispense the lavage fluid; and
   a warming component,
   wherein the body comprises a plurality of inner-channels having an inner surface configured to contact a corresponding outer surface of the warming component, and
   wherein the warming component comprises a warming material sufficient to warm the lavage fluid housed in the body using energy transferred from the warming material to the lavage fluid via the inner surface of the plurality of inner channels and the corresponding outer surface of the warming component.

2. The system according to claim 1, wherein the warming component comprises a surrounding channel portion configured to surround at least a portion of the lavage fluid in the body.

3. The system according to claim 1, wherein the warming material is configured to absorb energy.

4. The system according to claim 1, wherein the warming material comprises an activatable warming material configured to provide heat upon activation.

5. The system according to claim 1, wherein the warming material comprises a warming fluid.

6. The system according to claim 5, wherein the warming fluid comprises heated water.

7. The system according to claim 5, wherein the warming component comprises:
   an input configured for the warming fluid to enter the warming component, and
   an output configured for the warming fluid to exit the warming component.

8. The system according to claim 7, wherein at least one of the input and the output comprises a restrictive feature selected from the group consisting of a one-way valve and an actuatable valve.

9. The system according to claim 1, wherein the warming material is sufficient to warm the lavage fluid housed in the body to a temperature between about 32 and 43° C.

10. The system according to claim 9, wherein the warming material is sufficient to warm the lavage fluid housed in the body to the temperature in a heating period of no more than five minutes.

11. The system according to claim 9, wherein the system further comprises a temperature indicator configured to provide a signal when the lavage fluid has reached the temperature.

12. The system according to claim 11, wherein the signal comprises a change in color of a temperature-sensitive material.

13. The system according to claim 11, wherein the temperature indicator is comprised by at least one of the body and the warming component.

14. The system according to claim 1, wherein the lavage fluid comprises an antiseptic agent and water, the antiseptic agent comprising iodine.

* * * * *